United States Patent
Hoffman et al.

(10) Patent No.: US 10,589,134 B2
(45) Date of Patent: *Mar. 17, 2020

(54) HAND HEALTH AND HYGIENE SYSTEM FOR HAND HEALTH AND INFECTION CONTROL

(75) Inventors: Douglas Robert Hoffman, Greenville, WI (US); Scott W. Wenzel, Neenah, WI (US); David William Koenig, Menasha, WI (US); Lisa Flugge-Berendes, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1818 days.

This patent is subject to a terminal disclaimer.

(21) Appl. No.: 12/022,328

(22) Filed: Jan. 30, 2008

(65) Prior Publication Data

US 2009/0191248 A1 Jul. 30, 2009

(51) Int. Cl.
| | | |
|---|---|---|
| *A61Q 19/00* | (2006.01) | |
| *A61K 8/49* | (2006.01) | |
| *A61K 8/43* | (2006.01) | |
| *A61Q 17/00* | (2006.01) | |
| *A61K 8/86* | (2006.01) | |
| *A61K 8/60* | (2006.01) | |

(52) U.S. Cl.
CPC .............. *A61Q 19/00* (2013.01); *A61K 8/43* (2013.01); *A61K 8/4946* (2013.01); *A61K 8/602* (2013.01); *A61K 8/86* (2013.01); *A61Q 17/00* (2013.01); *A61K 2800/31* (2013.01)

(58) Field of Classification Search
None
See application file for complete search history.

(56) References Cited

U.S. PATENT DOCUMENTS

| | | |
|---|---|---|
| 3,301,746 A | 1/1967 | Sanford et al. |
| 3,338,992 A | 8/1967 | Kinney |
| 3,341,394 A | 9/1967 | Kinney |
| 3,473,576 A | 10/1969 | Amneus |
| 3,502,763 A | 3/1970 | Hartmann |
| 3,542,615 A | 11/1970 | Dobo et al. |
| 3,573,164 A | 3/1971 | Friedberg et al. |
| 3,675,121 A | 7/1972 | Thompson |
| 3,692,618 A | 9/1972 | Dorschner et al. |
| 3,802,817 A | 4/1974 | Matsuki et al. |
| 3,812,000 A | 5/1974 | Salvucci, Jr. et al. |
| 3,821,068 A | 6/1974 | Shaw |
| 3,849,241 A | 11/1974 | Butin et al. |
| 3,896,807 A | 7/1975 | Buchalter |
| 3,974,025 A | 8/1976 | Ayers |
| 4,011,389 A | 3/1977 | Langdon |
| 4,134,838 A | 1/1979 | Hooper et al. |
| 4,137,180 A | 1/1979 | Naik et al. |
| 4,191,609 A | 3/1980 | Trokhan |
| 4,208,459 A | 6/1980 | Becker et al. |
| 4,239,065 A | 12/1980 | Trokhan |
| 4,340,563 A | 7/1982 | Appel et al. |
| 4,347,931 A | 9/1982 | Ginger et al. |
| 4,528,239 A | 7/1985 | Trokhan |
| 4,637,859 A | 1/1987 | Trokhan |
| 4,720,415 A | 1/1988 | Vander Wielen et al. |
| 4,767,547 A | 8/1988 | Straathof et al. |
| 4,788,733 A | 12/1988 | Lerner |
| 4,789,491 A | 12/1988 | Chang et al. |
| 4,812,284 A | 3/1989 | Fleissner |
| 5,169,251 A | 12/1992 | Davis |
| 5,183,601 A * | 2/1993 | Jisai et al. ..................... 510/470 |
| 5,213,881 A | 5/1993 | Timmons et al. |
| 5,364,382 A | 11/1994 | Latimer et al. |
| 5,486,166 A | 1/1996 | Bishop et al. |
| 5,490,846 A | 2/1996 | Ellis et al. |
| 5,539,056 A | 7/1996 | Yang et al. |
| 5,596,052 A | 1/1997 | Resconi et al. |
| 5,607,551 A | 3/1997 | Farrington, Jr. et al. |
| 5,614,202 A | 3/1997 | DeFina |
| 5,639,532 A | 6/1997 | Wells |
| 5,690,918 A * | 11/1997 | Jacks ................... A61K 8/4913 424/401 |
| 5,849,314 A * | 12/1998 | Dobkowski .............. A61K 8/31 424/401 |
| 5,869,072 A | 2/1999 | Berry |
| 6,013,270 A | 1/2000 | Hargraves et al. |
| 6,037,281 A | 3/2000 | Mathis et al. |
| 6,103,245 A * | 8/2000 | Clark ....................... A61K 8/19 424/401 |
| 6,180,584 B1* | 1/2001 | Sawan et al. ................. 510/382 |
| 6,183,766 B1* | 2/2001 | Sine .................... A61K 8/0208 424/401 |
| 6,261,580 B1 | 7/2001 | Lehrier et al. |
| 6,274,154 B1 | 8/2001 | Chou |
| 6,383,999 B1 | 5/2002 | Coyle et al. |
| 6,423,328 B2 | 7/2002 | Chou |
| 6,500,443 B1 | 12/2002 | Otts et al. |
| 6,500,563 B1 | 12/2002 | Datta et al. |

(Continued)

FOREIGN PATENT DOCUMENTS

| | | |
|---|---|---|
| EP | 0032793 A2 | 7/1981 |
| EP | 0147146 A2 | 7/1985 |

(Continued)

OTHER PUBLICATIONS

Glove-balloon man, retrieved from <shanaynaynoelle.deviantart.com/art/GLOVE-BALLOON-MAN-190167354?moodonly> on May 2, 2011, pp. 1-6.*

(Continued)

*Primary Examiner* — David J Blanchard
*Assistant Examiner* — Ivan A Greene
(74) *Attorney, Agent, or Firm* — Armstrong Teasdale LLP

(57) ABSTRACT

The present disclosure is directed to a system and methods for maintaining or improving hand health and hygiene. More particularly, the system and methods prevent or overcome skin damage caused by frequent hand washing and use of hand sanitizers and/or cleansers. The hand care system comprises an article, such as an elastomeric glove, that has a moisturizing liquid liner composition on the skin-contacting surface of the article that delivers a skin health benefit to the skin, a non-irritating hand cleanser capable of moisturizing the skin, and a moisturizing hand sanitizer.

14 Claims, 2 Drawing Sheets

(56) References Cited

U.S. PATENT DOCUMENTS

| | | | |
|---|---|---|---|
| 6,513,998 | B1 | 2/2003 | Barry |
| 6,630,152 | B2 | 10/2003 | Chou |
| 6,638,587 | B1 | 10/2003 | Wang et al. |
| 6,896,766 | B2 | 5/2005 | Sarbo et al. |
| 6,953,582 | B2 | 10/2005 | Chou |
| 6,958,103 | B2 | 10/2005 | Anderson et al. |
| 6,960,349 | B2 | 11/2005 | Shantz et al. |
| 7,147,752 | B2 | 12/2006 | Shannon et al. |
| 2002/0006886 | A1* | 1/2002 | Beerse ............ A61K 8/0208 510/295 |
| 2003/0228351 | A1 | 12/2003 | Hasenochrl et al. |
| 2004/0067206 | A1* | 4/2004 | Paspaleeva-Kuhn ............ A61K 8/922 424/59 |
| 2004/0115250 | A1 | 6/2004 | Loo et al. |
| 2004/0122382 | A1* | 6/2004 | Johnson ............ A61L 31/16 604/292 |
| 2004/0126604 | A1 | 7/2004 | Wang et al. |
| 2004/0241201 | A1 | 12/2004 | Wang et al. |
| 2005/0079192 | A1 | 4/2005 | Simon |
| 2005/0081278 | A1 | 4/2005 | Williams |
| 2005/0106201 | A1* | 5/2005 | Janssen ............ 424/402 |
| 2005/0222543 | A1 | 10/2005 | Shao |
| 2005/0260147 | A1 | 11/2005 | Elliott et al. |
| 2006/0008621 | A1 | 1/2006 | Gusky et al. |
| 2006/0039938 | A1* | 2/2006 | Josse ............ 424/401 |
| 2006/0070167 | A1 | 4/2006 | Eng et al. |
| 2006/0074029 | A1 | 4/2006 | Leece |
| 2006/0143767 | A1 | 7/2006 | Yang et al. |
| 2007/0244203 | A1 | 10/2007 | Raul et al. |
| 2007/0259029 | A1 | 11/2007 | McEntire et al. |

FOREIGN PATENT DOCUMENTS

| | | |
|---|---|---|
| EP | 0591609 A1 | 4/1994 |
| EP | 0617164 A1 | 9/1994 |
| EP | 0677612 A2 | 10/1995 |
| EP | 1088540 | 4/2001 |
| EP | 1125540 A1 | 8/2001 |
| EP | 1266600 A1 | 12/2002 |
| EP | 1444970 A1 | 8/2004 |
| EP | 1454577 A2 | 9/2004 |
| FR | 2813777 B1 | 3/2002 |
| WO | 03022962 A2 | 3/2003 |
| WO | 2003105916 A1 | 12/2003 |
| WO | 2004043179 A2 | 5/2004 |
| WO | 2004043235 A2 | 5/2004 |
| WO | 2004060432 A1 | 7/2004 |
| WO | 2004108036 A1 | 12/2004 |
| WO | 2006110271 | 10/2006 |
| WO | 2007018822 A1 | 2/2007 |
| WO | 2007064343 A2 | 6/2007 |

OTHER PUBLICATIONS

McDonnell, Gerald and Russel, A. Denver; "Antiseptic and Disinfectants: Activity, Action, and Resistance", 1999, American Society for Microbiology; Clinical Microbiology Reviews, vol. 12, No. 1, pp. 147-179 and 227.*

Lewis, Sr. Richard J.; "Hawley's Condensed Chemical Dictionary," 2007, Wiley-Interscience; p. 854.*

Product information for ABIL® WE 09; EVONIK Industries, Feb. 2008, pp. 1-5.*

Reeth et al.; "Silicones: Enhanced Protection Across Personal Care Applications," 1998, Dow Corning S. A. Belgium; pp. 1-7, as provided.*

International Search Report and Written Opinion of PCT/162009/050240 dated Sep. 24, 2009.

European Search Report for Application No. 09794091 dated Jul. 4, 2013; 6 pages.

Office Action for Russian Application No. 2011104727/15 dated Dec. 14, 2012; 4 pages.

International Search Report and Written Opinion of International Application No. PCT/IB2009/052990, dated Mar. 2, 2010.

Kamath, et al., "Finishing of Nonwoven Bonded Fabrics," http://web.utk.edu/~mse/Textiles/Finishing%20of%20Nonwovens.htm, updated Apr. 2004, printed Aug. 5, 2008 (11 pages).

"Materials Science & Engineering 554, Nonwovens Science and Technology II," http://web.utk.edu/~mse/Textiles/index.html, Spring 2004, printed Aug. 5, 2008 (2 pages).

Gao, et al., "Thermal Bonding of Nonwoven Fabrics," Educational Research Nonwoven Thermal Bonding, http://www.apparelsearch.com/Education/Research/Nonwoven/2001_Kermit_Duckett/education_research_nonwoven_thermal_bonding.htm, 2001, printed Aug. 4, 2008 (10 pages).

Quack, R., et al., "Calender Processes in the Nonwoven Industry," International Nonwovens Technical Conference, INTC 2001, Sep. 5-7, 2001 (15 pages).

Scruggs, J., "A brief overview of the evolution of propylene fiber processes," Propylene Technology Conference, Aug. 31-Sep. 1, 1994 (10 pages).

Smith, P., "Nonwoven Fabric Machinery," Textile Horizons, vol. 12(2), pp. 34-35 (Feb./Mar. 1992).

Reddy, et al., "Stability Testing of O/W Emulsions Through Dielectric Constant-I," Cosmetics & Toiletries, vol. 99 (10), pp. 67-72 (Oct. 1984).

International Search Report and Written Opinion of International Application No. PCT/IB2009/052989, dated Feb. 26, 2010.

Non-final Office Action regarding U.S. Appl. No. 12/172,039, dated Dec. 8, 2011.

Non-final Office Action regarding U.S. Appl. No. 12/172,049, dated Dec. 23, 2010.

Final Office Action regarding U.S. Appl. No. 12/172,049, dated Jun. 9, 2011.

Office Action for Russian Application No. 2011104725/15 dated Nov. 23, 2012; 6 pages.

Patent Examination Report No. 1 for Patent Application No. 2009269612 dated Aug. 20, 2013; 5 pages.

Patent Examination Report No. 2 issued in Australian Patent Application No. 2009269611 (Dec. 16, 2013)(3 pages).

* cited by examiner

HAND HEALTH AND HYGIENE SYSTEM FOR HAND HEALTH AND INFECTION CONTROL

BACKGROUND OF THE DISCLOSURE

The present disclosure is directed to a system and method for maintaining or improving hand health and hygiene. More particularly, the system and methods prevent or overcome skin damage caused by frequent hand washing and use of hand sanitizers and/or cleansers. The hand health and hygiene system comprises an article, such as an elastomeric glove, that has a coating on the skin-contacting surface of the article that delivers a skin health benefit to the skin, a non-irritating hand cleanser capable of moisturizing the skin, and a moisturizing hand sanitizer.

Most healthcare workers are required to work with multiple patients throughout the course of a day. When moving from one patient to another most, if not all healthcare facilities require healthcare workers to follow a standard hand hygiene regimen. Generally, this regimen includes: (1) washing hands using cleanser and water or using a hand sanitizer product, (2) donning new gloves, (3) removing and discarding used gloves, and (4) washing hands using cleanser and water or using a hand sanitizer. While this regimen has benefits for preventing the spread of infection, it can be extremely damaging to the hands and skin of healthcare workers. In some instances, the damage can be to the degree that healthcare workers will not follow the hand hygiene regimen to avoid further damaging their skin. Unfortunately, non-compliance with this regimen has been shown to increase the spread of infections in healthcare settings.

It is documented that surgical or examination gloves can cause skin damage through friction, allergic reactions, and irritation from repeated use. Surgical and examination gloves are designed to be worn for short as well as extended periods of time. However, when gloves are worn for extended periods of time, body heat generated by the hand and perspiration can cause overhydration, which can damage the natural skin protection afforded by the stratum corneum. Overhydration may also lead to various other skin problems including, for example, growth of fungi and yeast as well as bacterial and viral infections of the skin. Additionally, after the gloves are removed from the hand and the sweat evaporates, the skin of the hand can become dry, sensitive, and sometimes ineffective. Furthermore, the gloves can exacerbate the skin damage caused by required clinical hand washing and/or sanitizing.

It would therefore be desirable to provide a hand hygiene regimen that maintains hand health in clinical settings, while simultaneously meeting the healthcare requirements for preventing the spread of healthcare associated infections. The present disclosure describes a hand health and hygiene system and products for maintaining optimal hand health in clinical settings. This system includes: (1) a glove or other skin contacting, substantially moisture impermeable article containing a moisturizing liquid liner composition; (2) a hand cleanser containing skin benefit ingredients, and (3) a hand sanitizer that provides skin health benefits for use when hand washing cannot be done.

SUMMARY OF THE DISCLOSURE

The present disclosure is directed to a system and method for maintaining or improving hand health and hygiene. More particularly, the system and methods prevent or overcome skin damage caused by frequent hand washing and use of hand sanitizers and/or cleansers. The hand care system comprises an article for contacting the skin of a wearer, such as an elastomeric glove, that has a coating on the skin-contacting surface of the article that delivers a skin health benefit to the skin, a non-irritating hand cleanser capable of moisturizing the skin, and a moisturizing hand sanitizer.

In one aspect, the present disclosure is directed to a hand health and hygiene system comprising: a glove comprising a flexible, substantially water impermeable substrate having a skin-contacting surface, and a moisturizing liquid liner composition applied to at least a portion of the skin contacting surface, the moisturizing liquid liner composition comprising a hydrophobic moiety and an emulsifier, wherein the moisturizing liquid liner composition is substantially anhydrous; and a moisturizing hand sanitizer.

In another aspect, the present disclosure is directed to a hand health and hygiene system comprising: a glove comprising a flexible, substantially water impermeable substrate having a skin-contacting surface, and a moisturizing liquid liner composition applied to at least a portion of the skin contacting surface, the moisturizing liquid liner composition comprising a hydrophobic moiety and an emulsifier, wherein the moisturizing liquid liner composition is substantially anhydrous; and a moisturizing hand cleanser.

In another aspect, the present disclosure is directed to a method for cleansing hands and providing a skin benefit to hands. The method comprises donning a glove comprising a flexible, substantially water impermeable substrate having a skin-contacting surface, and a moisturizing liquid liner composition applied to at least a portion of the skin contacting surface, the moisturizing liquid liner composition comprising a hydrophobic moiety and an emulsifier, wherein the moisturizing liquid liner composition is substantially anhydrous; cleansing the hands with a moisturizing hand cleanser; and sanitizing the hands with a moisturizing hand sanitizer.

Other objects and features will be in part apparent and in part pointed out hereinafter.

DETAILED DESCRIPTION OF THE DISCLOSURE

Figure 1:
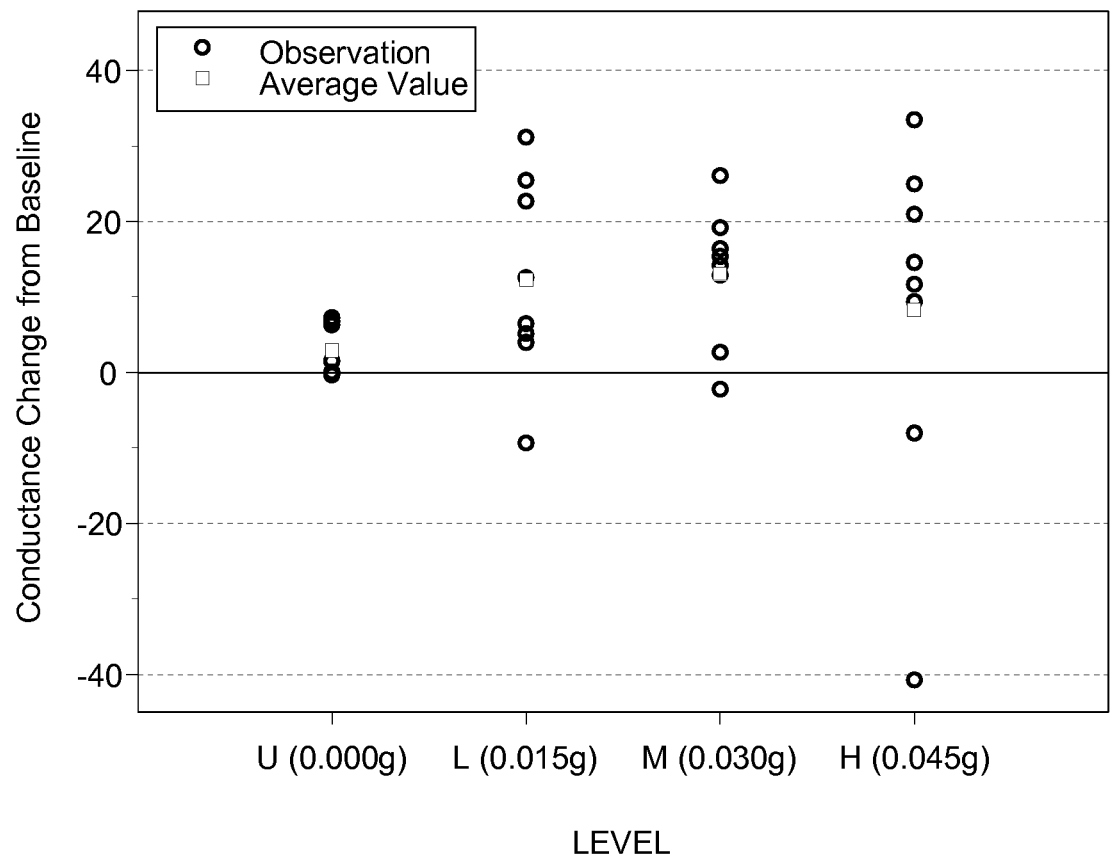
FIG. 1 is a chart illustrating percent change in conductance relative to a baseline measurement for four different glove treatments, as described in Example 2. The code "U" results are for the untreated control glove; the code "L" results are for the glove treated with an add-on amount of 0.015 grams moisturizing liquid liner composition per gram of glove; the code "M" results are for the glove treated with an add-on amount of 0.030 grams moisturizing liquid liner composition per gram of glove; and code "H" is for the glove treated with an add-on amount of 0.045 grams moisturizing liquid liner composition per gram of glove. The "○" indicates an actual conductance measurement, while "□" indicates the average of all conductance measurements for the particular glove treatment.

The present disclosure is directed to a system and method for maintaining or improving hand health and hygiene. More particularly, the system and methods prevent or overcome skin damage caused by frequent hand washing and use of hand sanitizers and/or cleansers. The hand health and hygiene system comprises an article for contacting the skin of a wearer, such as an elastomeric glove, that has a moisturizing liquid liner composition on the skin-contacting surface of the article that delivers a skin health benefit to the skin, a non-irritating hand cleanser capable of moisturizing the skin, and a moisturizing hand sanitizer.

As noted above, most healthcare workers are required to follow a standard hand hygiene regimen to prevent the spread of healthcare associated infections. Typically, this regimen involves washing the hands using a cleanser and water and/or use of a hand sanitizing product, donning new gloves, removing and discarding used gloves, and washing hands using a cleanser and water and/or using a hand sanitizer product. This process may be repeated multiple times during the course of a day. While this regimen is helpful in preventing the spread of infection, it oftentimes inflicts damage to the hands and skin of healthcare workers. For instance, extended wear of surgical or examination gloves may cause overhydration of the skin, which can damage the natural skin protection afforded by the stratum corneum and result in skin dermatitis and other skin irritations, and possible infections. Additionally, repeated use of hand sanitizers and/or cleansers may strip oils from the hands, leading to dry, irritated, and cracked skin.

The present disclosure addresses these issues by providing a hand health and hygiene system that counteracts the damaging effects of short and extended glove wear and hand cleansing and/or sanitizing. In particular, the hand health and hygiene system of the present disclosure provides an article, such as a glove or glove liner, which has applied to at least a portion of the skin-contacting surface thereof, a moisturizing liquid liner composition. The moisturizing liquid liner composition is a substantially anhydrous liquid composition that can transfer to the skin of the article's wearer, forming a hydrophobic coating on the skin. The coating may combine with moisture present in the skin to form a lotion-like water-in-oil emulsion upon contact with moisture present in the skin. The substantially anhydrous composition and/or the emulsion helps moisturize the skin and prevent skin dermatitis and other skin irritations that may otherwise occur as the result of extended wear of the article. The system additionally provides a non-irritating hand cleanser that both cleanses and moisturizes the skin, and a hand sanitizer that disinfects and moisturizes the skin.

The treated glove, hand cleanser, and hand sanitizer may be used singly, or in any combination thereof to prevent and overcome skin irritation and dryness typically associated with extended glove wear and hand cleansing and/or sanitizing. Advantageously, it has been found that in some instances, use of the moisturizing hand cleanser and/or moisturizing hand sanitizer described herein may in fact improve the effectiveness of the moisturizing liquid liner composition present on the skin-contacting surface of the treated glove by providing for better composition transfer to the skin, improved degree of emulsification, and longer-lasting moisturizing effects.

Thus, in one aspect, the present disclosure is directed to a hand health and hygiene system. The system comprises a glove comprising a flexible, substantially moisture impermeable substrate (also referred to herein as a "barrier layer") having a skin-contacting surface, and a moisturizing liquid liner composition applied to at least a portion of the skin contacting surface. The moisturizing liquid liner composition comprises a hydrophobic moiety, an emulsifier, and optionally a cationic moiety and/or an oil-soluble or oil-dispersible skin benefit agent, and is substantially anhydrous. The system further comprises a moisturizing hand sanitizer. In another aspect, the hand health and hygiene system may comprise the treated glove and a moisturizing hand cleanser. In yet another aspect, the hand health and hygiene system may comprise the treated glove, the moisturizing hand cleanser, and the moisturizing hand sanitizer.

The hand health and hygiene system of the present disclosure is particularly beneficial in the health care fields and food and beverage preparation and service industries, where frequent hand washing and glove wearing is oftentimes required.

Treated Article

As noted above, the hand health and hygiene system of the present disclosure may comprise an article for contacting the skin of a wearer, such as a glove, glove liner, and the like, which is to be worn by the wearer so that an inside portion of the article comes into direct contact with the wearer's skin. The article advantageously has a coating on the skin-contacting surface of the article. More particularly, the coating is a moisturizing liquid liner composition that may transfer to the skin of the article's wearer, forming a hydrophobic coating on the skin. The coating may combine with moisture present in the skin to form a water-in-oil emulsion. Preferably, the moisturizing liquid liner composition is substantially anhydrous. The substantially anhydrous coating and/or the emulsion helps moisturize the skin and prevent skin dermatitis and other skin irritations that may otherwise occur as the result of extended wear of the article.

The article generally comprises a moisture impermeable substrate (i.e., a barrier layer) comprising an outer surface which faces away from the skin and an inner, skin-contacting surface which comes into direct contact with the skin of the wearer. As noted above, the skin contacting surface of the article is coated with a moisturizing liquid liner composition. The moisturizing liquid liner composition, before addition of moisture thereto, is preferably in the form of a substantially anhydrous, liquid at room temperature, and generally comprises a hydrophobic moiety, an emulsifier, and optionally a cationic moiety and/or an oil-soluble or oil-dispersible skin benefit agent. Upon donning of the article, the moisturizing liquid liner composition may transfer to the skin of the article's wearer, forming a protective hydrophobic coating on the skin. In certain instances, moisture such as may be present in the skin of the article's wearer, may be added to the composition during article wear, thus forming a water-in-oil emulsion.

As noted above, the article will typically be a glove or glove liner, with the skin-contacting surface of the glove or glove liner coated with the moisturizing liquid liner composition to provide a hand care product. The glove or a pair of such gloves or liners may be used by themselves, for example, as surgical or examination gloves, rubber gloves, dress gloves, work gloves, gardening gloves, and the like, or as a separate liner under these gloves. The inner portion of the glove or liner which comes into direct contact with the skin of the wearer will carry the moisturizing liquid liner composition, which is the oil phase of the water-in-oil emulsion. Upon addition of moisture to the moisturizing liquid liner composition, the composition may form an emulsion. The moisture required to form the emulsion will in most cases be supplied by the wearer of the glove. Where the gloves are worn while working, for example, such as surgical or examination gloves worn during medical examinations or procedures, or rubber gloves worn during the washing of dishes, floors, and the like, the moisture and heat produced by perspiration of the hands and the occlusive glove environment will be sufficient to cause emulsification of at least a portion of the oil phase present on the skin-contacting surface of the glove, to form a therapeutic, lotion-like water-in-oil emulsion. Since the emulsion forms while the gloves are being worn, the emulsion will work into the pores of the skin to provide beneficial and therapeutic effects even after the gloves are removed. The emulsion may thus act to moisturize and protect the skin, and provide a pleasant skin feel during and after glove wear.

Thus, in accordance with one aspect of the present disclosure, the hand health and hygiene system of the present disclosure provides an article for contacting the skin of a wearer. The article comprises a flexible, substantially moisture impermeable substrate (i.e., a "barrier layer") having a skin contacting surface, and a substantially anhydrous moisturizing liquid liner composition applied to at least a portion of the skin contacting surface. In one particularly preferred embodiment, the article is a glove or glove liner, and acts as a hand care product to provide a therapeutic skin benefit for the glove wearer. Such a product will have particular benefit in the medical and healthcare fields and/or food or beverage preparation industry where frequent hand washing and glove wearing is typically required.

The articles of the present disclosure may be prepared by depositing a layer of the moisturizing liquid liner composition on at least a portion of a skin-contacting surface of the article. The moisturizing liquid liner composition may generally be deposited on a surface of the article that will be in contact with epithelial tissue during use, where the moisturizing liquid liner composition may then provide a skin health benefit to the wearer of the article. In one embodiment, this surface may be at least a portion of the donning surface (the inside surface) of a glove.

In another embodiment, the moisturizing liquid liner composition may be deposited on at least a portion of the gripping surface (the outside surface) of the article and/or on more than one surface of the article, such as the inside and outside surface of the article. For example, the composition may be deposited on the donning surface of a medical glove to deliver a benefit to the skin of the wearer, and also be deposited on the gripping surface of the glove to deliver a benefit to the epithelial tissue of a patient. Moreover, the coatings on the two sides of the gloves may include different additives and deliver different benefits to the contacting tissue.

Examples of suitable articles for use with the present disclosure include gloves, such as surgical gloves, examination gloves; glove liners; lotions; wipes, and the like. Preferably, the article is a glove or glove liner, and more preferably is a medical glove such as a surgical or examination glove. Although discussed primarily herein in terms of a medical glove, such as a surgical or examination glove, it should be understood that the article of the present disclosure is not intended to be limited to medical gloves, and may also be other skin-contacting articles, such as glove liners, feminine pads, undergarments, face masks, patches, socks, bandages, wraps, gowns, drapes, caps, and the like.

The article will typically comprise a flexible, substantially moisture impermeable substrate (i.e., a barrier layer). The moisture impermeable nature of the barrier layer will trap perspiration from the skin in the article, where it will contact the moisturizing liquid liner composition and form the therapeutic water-in-oil emulsion. In one aspect, the article may have an elastomeric substrate. Elastomeric substrates are particularly useful when the article is a glove, as it is oftentimes desirable for the glove to be able to stretch to provide for easier glove donning. The article may be formed from a natural or a synthetic latex or a dissolved elastomeric polymer. For instance, the article may be formed of a natural or synthetic rubber, a nitrile rubber, a nitrile butadiene rubber, a polyisoprene, a polychloroprene, a polyurethane, a neoprene, a homopolymer of a conjugated diene, a copolymer of a least two conjugated dienes, a copolymer of at least one conjugated diene and at least one vinyl monomer, styrene block copolymers, or any other suitable combinations thereof. Examples of suitable synthetic rubbers can also include acrylic diene block co-polymers, acrylic rubber, butyl rubber, EPDM rubber, polybutadiene, chlorosulfonated polyethylene rubber, and fluororubber. Typically, the flexible, substantially moisture impermeable substrate of the article will be selected from the group consisting of latex, vinyl, a nitrile, and combinations thereof. Additionally, combinations of polymers or copolymers may be in a single layer of an article or in separate layers, such as in a multi-layer article.

In general, the articles of the present disclosure may be formed by any suitable process. For example, an elastomeric glove may be formed by a series of dipping processes of a former of the shape of the finished article, such as described in WO 2004/060432, herein incorporated by reference. Specifically, a former may generally be a contoured mold having a textured or smooth surface that may accept a series of coatings and release the formed article. The surface of the former may be ceramic, porcelain, glass, metal, or formed from certain fluorocarbons.

If desired, a former may be cleaned prior to formation of a glove on the former. The cleaning process may generally include an optional water pre-rinse followed by an acid wash. After the acid wash, the former may be rinsed with water and dipped in a heated caustic solution prior to a final water rinse. After the cleaning process, a glove may be formed on the former through a series of dipping and drying steps.

In one embodiment, the glove may be formed through a series of dippings or immersions of the former. For example, in one embodiment, after cleaning, the former may be dipped into a coagulant composition prior to forming the main body or substrate of the glove on the former. For purposes of this disclosure, the substrate of the glove is intended to mean the main body of the glove and includes one or more layers of material. The coagulant causes the base polymer which forms the substrate of the glove to coagulate. Coagulant compositions that may be used in the present disclosure may include powders to ease stripping of the glove from the former, or, if desired, may be powder free. In one embodiment, a powder free coagulant composition may be used which includes water soluble salts of calcium, zinc, aluminum, and the like. For example, calcium nitrate in water or alcohol may be used in the coagulant composition. In such an embodiment, calcium nitrate may be present in the solution in an amount of up to about 40% by weight. The coagulant composition may contain other additives, such as surfactants, that may improve the characteristics of the glove.

After being immersed in the coagulant composition, the former may be withdrawn and the coagulant present on the surface of the former allowed to dry.

Once dried, a residual coating of the coagulant is left on the former. The former may then be immersed or dipped into a latex bath of the desired elastomeric polymer. A latex is defined for the purposes of this invention as a colloid in which the elastomeric polymer is suspended in water.

In general, the latex bath of the present invention may have a dry rubber content (DRC) of less than about 50% or alternatively a total solid content (TSC) of less than about 50%. In one embodiment, the latex bath may have a DRC or a TSC content of less than about 25%. The latex bath may also contain various additives such as pH adjustors, stabilizers, and the like.

Upon contact of the latex with the coagulant composition, the coagulant causes some of the latex to become locally unstable and coagulate on the surface of the former. Any additives in the coagulant composition may, depending upon what they are, form a layer between the former and the latex film, or alternatively may be incorporated into the latex film and may subsequently be removed during a leaching process. After the desired amount of time, the former is withdrawn from the latex bath, and the coagulated layer is allowed to coalesce fully on the former.

The amount of time the former is immersed in the emulsion (commonly termed "dwell time") determines the thickness of the film. Increasing the dwell time of the former in the latex causes the thickness of the film to increase. The total thickness of the film forming the substrate may depend on other parameters, including, for example, the solids content of the latex emulsion and the additive content of the latex emulsion and/or the coagulant composition.

In other embodiments, the article may be formed from one or more polymers that have been dissolved in a suitable solvent and then allowed to dry on a former in the desired shape. For example, one or more elastomeric block copolymers as are generally known in the art may be dissolved in a solvent, such as toluene, and may then be dried or cured on a former in the shape of the desired elastomeric article. Suitable block copolymers include, for example, styrene-isoprene-styrene (S-I-S) block copolymers, styrene-polybutadiene-styrene (S-B-S) block copolymers, styrene-butadiene (S-B) block copolymers, styrene-ethylene butylene-styrene (S-EB-S) block copolymers, and mixtures thereof.

After formation of the first elastomeric polymer layer, the former may then be heated to gel the polymer. The former may then be rinsed in order to leach residual chemicals from the gelled polymer.

Where desired, additional polymer layers may be formed on the first layer, such that the substrate of the glove includes multiple layers. Such a process is generally termed an over-dip process. In one embodiment, an over-dip process may be carried out by immersing the former into an emulsion or a solution of the desired polymer. Additional layers of the primary matrix may enhance certain characteristics of the glove. For instance, an additional layer may provide an improved gripping surface or an improved donning surface on a finished glove. As such, an additional polymer layer which may improve donning of the glove may be a donning layer, and the moisturizing liquid liner composition of the present disclosure may subsequently be deposited on the donning layer.

Following formation of any additional polymeric layers in the substrate of the article, a bead rolling operation may be completed.

After the substrate of the article is formed including any desired overcoats, the substrate of the glove may be finally cured or vulcanized. In general, a natural latex rubber article may be vulcanized at a temperature of between about 80° C. and about 120° C. for from about 10 minutes to about 20 minutes, and a nitrile rubber article may be vulcanized at a temperature of between about 80° C. and about 150° C. for from about 10 minutes to about 20 minutes. In some embodiments, a natural or synthetic rubber latex may be vulcanized by high temperature reaction with a vulcanizing agent, generally sulfur, to cause crosslinking of the polymer chains. In addition to vulcanizing the latex, the high temperature process may cause the evaporation of any volatile components remaining on the former, such as any remaining water, for example. After vulcanization, the glove may be rinsed with water.

In some embodiments, the glove may be stripped from the former and subjected to a halogenation process, such as, for example, chlorination, to improve the surface characteristics of the glove, for example donning slip characteristics.

Chlorination may also remove residual proteins and, where a powdered coagulant is used, halogenation may remove residual powder from the surface of the glove. The glove may be chlorinated through immersion and optional agitation in an aqueous solution containing dissolved chlorine. In one embodiment, several gloves may be tumbled in a chlorine solution for a period of time between about 10 minutes and about 20 minutes.

After the optional halogenation process, the glove may be rinsed once more in water (preferably soft water) and dried prior to deposition of the presently disclosed moisturizing liquid liner composition. For example, a two-step drying process may be utilized in which the gloves are first partially dried by spin-drying in an extractor and then completely dried by being placed in a cyclone dryer.

After drying, the moisturizing liquid liner composition of the present disclosure may be applied to at least one surface of the glove. The composition may be applied to at least a portion of the skin-contacting surface of the glove and may contain a hydrophobic moiety, an emulsifier, and optionally a cationic moiety and/or an oil-soluble or oil-dispersible skin benefit agent that may provide a health benefit to epithelial tissue, as well as other optional additives.

As indicated above, the moisturizing liquid liner composition is the oil phase of a water-in-oil emulsion that may form when the composition contacts moisture present in the skin of the article's wearer. The contact of the wearer's skin with the moisturizing liquid liner composition will produce sufficient moisture and heat to cause emulsification of at least a portion of the moisturizing liquid liner composition, and formation of a lotion-like emulsion that has moisturizing and other skin health benefit effects on the skin of the article's wearer. The beneficial effects of the emulsion can be felt both during article wear, after the article, such as a glove, is removed, and after subsequent washing of the skin. Advantageously, the emulsification of the moisturizing liquid liner composition may occur even after relatively short glove wear times, for example, of about 1 minute. The articles of the present disclosure are thus particularly useful in healthcare and food preparation settings where frequent hand washing oftentimes causes skin irritation and drying.

As noted above, the moisturizing liquid liner composition can absorb moisture from skin or moisture that results from the occlusive glove environment (e.g., up to about 90% (by weight of the composition) water) to form the emulsion. Although the moisturizing liquid liner composition may comprise some water, typically the moisturizing liquid liner composition of the present disclosure is applied to the glove as a substantially anhydrous composition. As used herein, "substantially anhydrous" is intended to mean the composition comprises water in an amount of about 5% (by weight of the composition) or less. Preferably, water is present in the composition in an amount of about 1% (by weight of the composition) or less, and more preferably about 0.5% (by weight of the composition) or less. More preferably, the composition is anhydrous (i.e., comprises 0% (by weight of the composition) of water). Because the moisturizing liquid liner composition is substantially anhydrous, oil soluble or oil-dispersible skin benefit agents may readily be dispersed into the composition. Additionally, because the moisturizing liquid liner composition is substantially anhydrous, when applied to the article there is no need to subject the composition to an additional drying step to remove aqueous composition components, which is typically required for glove coating compositions containing aqueous components.

The moisturizing liquid liner composition of the present disclosure is typically present on the article in a liquid form. Without wishing to be bound to any particular theory, it is believed the composition remains on the article rather as a result of hydrophobic interactions between the composition and the article surface. These hydrophobic interactions prevent the liquid composition from flowing or dripping off of the article prior to donning.

The moisturizing liquid liner composition may comprise a variety of components suitable for inclusion into an oil phase of a water-in-oil emulsion. Preferably, the composition components will be compatible with the article substrate and will not have any deleterious effects on the integrity of the substrate. In one aspect, the composition comprises a hydrophobic moiety, an emulsifier, and optionally a cationic moiety and/or an oil soluble or oil-dispersible skin benefit agent, and other optional components.

As noted above, the moisturizing liquid liner composition comprises a hydrophobic moiety. The hydrophobic moiety according to the present disclosure is not particularly limited but typically comprises a silicone oil in an amount which is at least 30 wt. %, more preferably at least 40 wt. %, even more preferably at least 50 wt. % of the hydrophobic moiety. The silicone oil is a liquid oil having a silicon backbone such as a $C_{1-22}$ dialkyl polysiloxane such as a dimethicone. Further, the backbone may have grafted onto it, $C_{1-22}$ alkyl groups, preferably $C_{4-22}$ alkyl groups, and more preferably cetyl groups. The silicone oil will preferably have a molecular weight ranging from 700 to 20,000, more preferably 800 to 14,000, more preferably 900 to 1,000, and more preferably about 1,000. The siloxane backbone of the silicone oil is not particularly limited and may range from about 5 to about 100 siloxane units.

In addition to the silicone oil, the hydrophobic moiety may further comprise a hydrophobic oil which is miscible with the silicone oil, such as hydrocarbon oils, dialkyl ethers, alkyl carboxylates, and alkoxylate ethers and esters.

Non-limiting examples of suitable hydrophobic oils include PPG-15 stearyl ether, dicaprylylether, diethylhexyl carbonate, $C_{12-15}$ alkyl benzoate, ethylhexyl palmitate, hexyldecyl stearate, isocetyl palmitate, isopropyl laurate, isopropyl palmitate, caprylic/capric triglyceride, triisostearin, propylene glycol myristyl ether, bis-PEG/PPG-20/20 dimethicone, PEG/PPG-4/12 dimethicone, cetyl palmitate, stearyl palmitate, cetyl stearate, isopropyl laurate, isopropyl myristate, isopropyl palmitate, caprylic/capric triglyceride, and combinations thereof. Ethers such as eucalyptol, ceteraryl glucoside, dimethyl isosorbic polyglyceryl-3 cetyl ether, polyglyceryl-3 decyltetradecanol, and propylene glycol myristyl ether may also be used.

Suitable silicone oils are well known to those of ordinary skill in the art and include comb-like modified siloxanes such as ABIL® EM90, ABIL® Wax 9801, ABIL® Wax 9814, and ABIL® Wax 9840, products of Evonik Degussa, alkyl dimethicones, alkyl methicones, alkyl dimethicone copolyols, phenyl silicones, alkyl trimethylsilanes, dimethicone, dimethicone crosspolymers, cyclomethicone, and combinations thereof. Preferably, the hydrophobic moiety is a cetyl dimethicone, such as ABIL® Wax 9801.

The amount of hydrophobic moiety in the moisturizing liquid liner composition is not particularly limited, and is typically present in an amount of from about 20% (by weight of the composition) to about 70% (by weight of the composition), more preferably from about 40% (by weight of the composition) to about 60% (by weight of the composition), and even more preferably about 50% (by weight of the composition).

The hydrophobic moiety may further comprise an auxiliary silicone oil such as cyclomethicone, in amounts up to 50% (by weight of the composition), and preferably from about 30% (by weight of the composition) to about 46% (by weight of the composition), in order to reduce the viscosity of the moisturizing liquid liner composition. A reduced viscosity allows the liquid liner layer to display enhanced spreadability, providing for easier application to the surface of a barrier layer.

The moisturizing liquid liner composition may further include one or more emulsifier. As noted above, the moisturizing liquid liner composition of the present disclosure is the oil phase of a water-in-oil emulsion that forms upon contact of the composition with water produced through perspiration of the skin or as a result of the occlusive environment produced when the article is worn. Inclusion of an emulsifier into the moisturizing liquid liner composition assists with the formation of a stable lotion-like emulsion upon contact of the moisturizing liquid liner composition with moisture. Typically, emulsifiers are molecules with non-polar and polar regions that are able to reside at the interface of the water and oil components of the emulsion.

Emulsifiers according to the present disclosure are not particularly limited and will preferably have a hydrophilic/lipophilic balance (HLB) of from 3 to 8, and behave as water-in-oil emulsifiers. Any suitable emulsifier may be included in the moisturizing liquid liner compositions of the present disclosure including carbon based emulsifiers, silicon based emulsifiers, non-ionic emulsifiers, cationic emulsifiers, and combinations thereof. Suitable carbon based emulsifers include polyglyceryl-4 isostearate. Silicon based water-in-oil emulsifers include alkylene oxide graft modified silicone oils. Suitable alkylene oxides include ethylene oxide, propylene oxide, butylene oxide, and mixtures thereof. Grafting of alkylene oxide groups may occur randomly or in blocks. Preferably, the grafting is block grafting of ethylene oxide and propylene oxide in a weight ratio of 10 to 1. Other emulsifers include Bis-PEG/PPG-14/14 dimethicone (ABILOEM 97, available from Evonik), polyglyceryl-3 oleate (ISOLAN® GO 33, available from Goldschmidt), polyglyceryl-4 diisostearate/polyhydrosysteate/sebacate (ISOLAN® GPS, available from Goldschmidt), polyglyceryl-2 dipolyhydroxystearate, polyglyceryl-3 polyricinoleate, PEG-30 dipolyhydroxystearate, glyceryl stearate, hydrogenated vegetable glycerides phosphate, soribitan oleate, sorbitan sessquioleate, sorbitan isostearate, sorbitan trioleate, polyglyceryl-3-diisostearate, polyglyceryl-4 oleate, or combinatiosn thereof.

The emulsifier may be used alone, or in combination with other emulsifiers. Preferably, the emulsifier is a mixture of polyglyceryl-4 isostearate, cetyl PEG/PPG-10/1 dimethicone, and hexyl laurate, sold under the trademark ABIL® WE 09 (available from Evonik).

The amount of emulsifier in the moisturizing liquid liner composition is not particularly limited and is typically present in an amount of from about 0.4% (by weight of the composition) to about 10% (by weight of the composition), preferably from about 1% (by weight of the composition) to about 8% (by weight of the composition), more preferably from about 3% (by weight of the composition) to about 6% (by weight of the composition), and more preferably from about 4% (by weight of the composition) to about 5% (by weight of the composition).

In use, the hydrophobic moiety, in conjunction with the emulsifier, forms an occlusive layer on the skin.

The moisturizing liquid liner composition may optionally be formulated to have a net cationic charge, and may further comprise one or more cationic moiety. Without wishing to be bound by any particular theory, it is believed that by formulating the composition to have a net cationic charge, the composition will interact with negatively charged sites on the skin, thus improving the transfer of the moisturizing liquid liner composition (and water-in-oil emulsion that may be formed upon contact of the composition with moisture) from the article to the skin of the wearer. Suitable cationic moieties according to the present invention are not particularly limited and are typically those used as fabric softeners.

Hydrocarbon fabric softeners suitable for use herein are selected from the following classes of compounds.

Cationic quaternary ammonium salts: The counter ion of cationic quaternary ammonium salts may be a halide, such as chloride or bromide, methyl sulphate, or other ions well known in the literature. Preferably, the counter ion is methyl sulfate or any alkyl sulfate or any halide, with methyl sulfate being most preferred.

Examples of cationic quaternary ammonium salts include, but are not limited to conventionally known monoalkyl quaternary ammonium salts, dialkyl quaternary ammonium salts, and tetra-alkyl quaternary ammonium salts, such as:

(1) Acyclic quaternary ammonium salts having at least two $C_8$ to $C_{30}$, and preferably $C_{12}$ to $C_{22}$ alkyl or alkenyl chains, such as: dimethyl ditallow ammonium methylsulfate, di(hydrogenated tallow)dimethyl ammonium methylsulfate, distearyldimethyl ammonium methylsulfate, dicocodimethyl ammonium methylsulfate, and the like. It is especially preferred if the cationic moiety is a water insoluble quaternary ammonium material which comprises a compound having two $C_{12}$ to $C_{18}$ alkyl or alkenyl groups connected to the molecule via at least one ester link. It is more preferred if the quaternary ammonium material has two ester links present. An especially preferred ester-linked quaternary ammonium material for use in the invention can be represented by the formula:

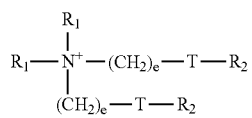

wherein each $R_1$ group is independently selected from $C_1$ to $C_4$ alkyl, hydroxyalkyl, or $C_2$ to $C_4$ alkenyl groups; T is either

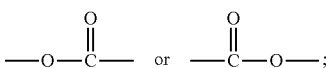

each $R_2$ group is independently selected from $C_8$ to $C_{28}$ alkyl or alkenyl groups; and e is an integer from 0 to 5.

A second preferred type of quaternary ammonium material can be represented by the formula:

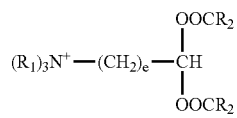

wherein $R_1$, e, and $R_2$ are as defined above.

(2) Cyclic quaternary ammonium salts of the imidazolinium type such as di(hydrogenated tallow)dimethyl imidazolinium methyl sulfate, 1-ethylene-bis(2-tallow-1-methyl)imidazolinium methyl sulfate, and the like.

(3) Diamido quaternary ammonium salts such as: methylbis(hydrogenated tallow amidoethyl)-2-hydroxethyl ammonium methyl sulfate, methyl bi(tallowamidoethyl)-2-hydroxypropyl ammonium methylsulfate, and the like.

(4) Biodegradable quaternary ammonium salts such as N,N-di(tallowoyl-oxy-ethyl)-N,N-dimethyl ammonium methyl sulfate, and N,N-di(tallowoyl-oxy-propyl)-N,N-dimethyl ammonium methyl sulfate. Biodegradable quaternary ammonium salts are described in, for example, U.S. Pat. Nos. 4,137,180, 4,767,547, and 4,789,491.

Preferred biodegradable quaternary ammonium salts include biodegradable cationic diester compounds, such as those described in U.S. Pat. No. 4,137,180.

Cationic moieties are further described in U.S. Pat. No. 4,134,838.

In addition, the cationic moiety may be a cationically modified silicone based surfactant, such as those known in the art and including, for example, silicone bissquaternary compounds. Suitable bisquaternary compounds may have a siloxane backbone of 10 to 100, and preferably 60 to 100 silixane units, which are terminally modified with quaternary ammonium groups at each end. In one embodiment, the terminal ends of the bisquaternary compound is comprised of alkyl amide quaternary ammonium hydroxyl groups such as those resulting from ring opening of an epoxide with an alkyl amide amine. Preferably, the cationic moiety is a silicone bisquaternary, such as quaternium-80, available commercially under the name ABIL® Quat 3474 (available from Evonik).

To the extent that the components of the moisturizing liquid liner composition comprise salt forming groups, such as the silicone bisquaternary compounds, the moisturizing liquid liner layer may comprise salts of such salt forming groups. Suitable salts are known to those of ordinary skill in the art and include acetate salts of quaternary ammonium groups.

Other examples of suitable cationic moieties include polyquaternium-7, polyquaternium-10, benzalkonium chloride, behentrimonium methosulfate, cetrimonium chloride, cocamidopropyl pg-dimonium chloride, guar hydroxypropyltrimonium chloride, isostearamidopropyl morpholine lactate, polyquaternium-33, polyquaternium-60, polyquaternium-79, quaternium-18 hectorite, quaternium-79 hydrolyzed silk, quaternium-79 hydrolyzed soy protein, rape seed amidopropyl ethyldimonium ethosulfate, silicone quaternium-7, stearalkonium chloride, palmitamidopropyltrimonium chloride, butylglucosides, hydroxypropyltrimonium chloride, laurdimoniumhydroxypropyl decylglucosides chloride, quaternium-80, and the like.

The amount of cationic moiety in the moisturizing liquid liner composition is not particularly limited and is typically present in an amount of from about 0.01% (by weight of the composition) to about 10% (by weight of the composition), preferably from about 0.5% (by weight of the composition) to about 8% (by weight of the composition), more preferably from about 1% (by weight of the composition) to about 5% (by weight of the composition, and even more preferably about 1% (by weight of the composition).

The moisturizing liquid liner composition may further comprise components which do not adversely affect the composition, such as carrier/emollients, oil-soluble or oil-dispersible skin benefit components, and various other components.

Particular examples of suitable carriers/emollients that can be incorporated into the moisturizing liquid liner compositions of the present disclosure include oils such as petrolatum based oils, petrolatum, vegetable based oils, mineral oils, natural or synthetic oils, alkyl dimethicones, alkyl methicones, alkyldimethicone copolyols, phenyl silicones, alkyl trimethylsilanes, dimethicone, cetyl dimethicone, dimethicone crosspolymers, cyclomethicone, lanolin and its derivatives, fatty esters, glycerol esters and derivatives, propylene glycol esters and derivatives, alkoxylated carboxylic acids, fatty acids, other silicones, and combinations thereof.

In one particular aspect, the carrier/emollient may be a silicone, such as those selected from the group consisting of alkyl dimethicones, alkyl methicones, alkyl dimethicone copolyols, phenyl silicones, alkyl trimethylsilanes, dimethicone, dimethicone crosspolymers, cyclomethicone, and combinations thereof. Preferably, the silicone is selected from the group consisting of cyclomethicone, cetyl dimethicone, and combinations thereof.

Suitable esters could include, but not be limited to, cetyl palmitate, stearyl palmitate, cetyl stearate, isopropyl laurate, isopropyl myristate, isopropyl palmitate, caprylic/capric triglyceride, and combinations thereof. Ethers such as eucalyptol, ceteraryl glucoside, dimethyl isosorbic polyglyceryl-3 cetyl ether, polyglyceryl-3 decyltetradecanol, propylene glycol myristyl ether, and combinations thereof can also suitably be used as emollients.

The moisturizing liquid liner composition may include one or more carrier/emollient in an amount of from about 0.7% (by weight of the composition) to about 99% (by weight of the composition), more desirably from about 10% (by weight of the composition) to about 97% (by weight of the composition), more desirably from about 30% (by weight of the composition) to about 95% (by weight of the composition), and more desirably from about 60% (by weight of the composition) to about 95% (by weight of the composition).

The moisturizing liquid liner compositions of the present disclosure may further comprise a skin benefit agent. The skin benefit agent may be any composition component that provides a beneficial effect on the skin of the wearer. Preferably, the skin benefit agent is oil-soluble and/or oil-dispersible, to allow for ease of dispersion in the composition.

One example of a suitable skin benefit agent includes skin conditioning agents. Skin conditioning agents include agents that may help the skin retain moisture, improve softness, or improve texture. Skin conditioning agents include, for example, amino acids, including alanine, serine, and glycine; allantoin, keratin, and methyl glucose dioleate; alpha-hydroxy acids, including lactic acid and glycolic acid, which act by loosening dead skin cells from the skin's surface; moisturizers (agents that add or hold water in dry skin), including echinacea (an extract of the coneflower plant), shea butter, and certain silicones, including cyclomethicone, dimethicone, and simethicone; exfoliation agents; lubricants; skin-firming agents; anti-callous agents; anti-acne agents; anti-aging agents; anti-wrinkle agents; anti-dandruff agents; wound care agents; skin lipids; enzymes; scar care agents; humectants; powders; botanical extracts; and drugs.

Examples of suitable moisturizers include humectants; natural oils such as jojoba oil; synthetic oils such as mineral oil; silicones such as dimethicone; waxes such as beeswax; and the like.

Other skin benefit agents that may be suitable for use with the present disclosure include antioxidants, a unique group of substances that protect the body or other objects from oxidizing. Antioxidants prevent or slow the oxidation process, thereby protecting the skin from premature aging. Exemplary antioxidants for use in the present disclosure include ascorbic acid ester, vitamin C (ascorbic acid), vitamin E (lecithin), Alpha-Glycosyl Rutin (AGR, or Alpha Flavon, a plant-derived antioxidant), and coenzyme Q10 (also known as ubiquinone).

Other skin benefit agents which may be delivered to the skin during use include cheating agents, such as EDTA; absorptive/neutralizing agents, such as kaolin, hectorite, smectite, or bentonite; other vitamins and vitamin sources and derivatives, such as panthenol, retinyl palmitat, tocopherol, and tocopherol acetate; and anti-irritants such as chitin and chitosan.

Examples of botanical agents or extracts that may be suitable for use with the present disclosure include almonds, chamomile extracts such as bisabolol (believed to relieve irritation, swelling and itching in the skin), elder flowers, honey, safflower oil, and elastin (safflower oil and elastin are believed to aid in retaining skin elasticity).

In one embodiment, the skin benefit agent may be held in the moisturizing liquid liner composition in liposomes. A liposome is a vehicle for delivering agents to the skin. More specifically, a liposome is a microscopic sphere formed from a fatty compound, a lipid, surrounding a water-based agent, such as a moisturizer or an emollient. When the liposome is rubbed into the skin, it releases the agent throughout the stratum corneum.

In another embodiment, the beneficial agent may be present in the carrier in the form of a microencapsulant. A microencapsulant is a sphere of an emollient surrounded by a gelatin membrane that prevents the emollient from reacting with other ingredients in the composition and helps distribute the emollient more evenly when pressure is applied and the membrane is broken. The process of forming these beads is called microencapsulation and is generally known in the art.

The skin benefit agent may be present in the composition in an amount of from about 0.01% (by weight of the composition) to about 99% (by weight of the composition), and more desirably in an amount of from about 0.1% (by weight of the composition) to about 50% (by weight of the composition).

In addition to the other composition components, the moisturizing liquid liner composition may further comprise film forming agents, occlusive agents, and the like.

Optionally, the moisturizing liquid liner composition may further comprise components that improve composition properties including, for example, dyes, fragrances, and combinations thereof. Optionally, the composition may further comprise preservatives, however, since the composition is substantially anhydrous, additional preservatives are not required.

In one embodiment, the moisturizing liquid liner composition does not comprise an α hydroxyl lactone. In another embodiment, the moisturizing liquid liner composition does not comoprise a polyhydric alcohol. In another embodiment, the moisturizing liquid liner composition does not comprise a self-emulsifying wax as described in U.S. Patent Application No. 2004/0122382. In another embodiment, the moisturizing liquid liner composition does not comprise a mixture of a fatty alcohol, a fatty acid, and/or a fatty ester with a $C_{20}$ surfactant. In another embodiment, the moisturizing liquid liner composition does not comprise any of a cellulose, collagen, and/or a vinyl pyrolidone derived cationic polymer. In another embodiment, the moisturizing liquid liner layer does not comprise a silicone wax.

The moisturizing liquid liner composition may be applied to the skin-contacting and/or outer-facing surface of the article using any suitable means such as spray, dip, or tumble application. It has advantageously been discovered that the moisturizing liquid liner compositions of the present disclosure may be applied to the article substrate in relatively low add-on amounts while still obtaining good moisturization and skin benefit effects. Typically, the composition will be applied to the substrate of the article in an add-on amount of from about 0.01 mg/cm$^2$ to about 10 mg/cm$^2$, more preferably from about 0.1 mg/cm$^2$ to about 1 mg/cm$^2$, and more preferably from about 0.3 mg/cm$^2$ to about 0.5 mg/cm$^2$.

Hand Cleanser

As noted above, the hand health and hygiene system of the present disclosure may further comprise a hand cleanser. The cleanser may act to remove soils such as dirt, contaminants, microbes, or other debris from the hands. Advantageously, the cleanser may further comprise moisturizers and other skin benefit agents that may provide a moisturizing and soothing effect on skin. The cleanser may be used prior to or after use of the treated glove and/or hand sanitizer.

Generally, the cleanser for use in the hand health and hygiene system of the present disclosure can contain one or more surfactants. The surfactant contributes to the overall cleansing and emulsification properties of the cleanser. In addition, the cleansing composition can contain emollients, carriers, moisturizers, sequestrants, non-aqueous solvents, preservatives, pH modifiers, anti-microbial agents, disinfectants, fragrances, dyes, rheology modifiers, thickeners, and various other optional ingredients.

As described above, the cleanser includes one or more surfactants. Nonionic surfactants, anionic surfactants, cationic surfactants, betaines, sultaines, amphoteric surfactants, zwitterionic surfactants, imidazolines, sulfosuccinates, amino oxides, alkanolamides, and combinations thereof may all be suitable for use in the present disclosure.

Nonionic surfactants typically have a hydrophobic base, such as a long chain alkyl group or an alkylated aryl group, and a hydrophilic chain comprising a certain number (e.g., 1 to about 30) of ethoxy and/or propoxy moieties. Examples of some classes of nonionic surfactants that can be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, and mixtures thereof.

Various specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty (C—$C_{22}$) alcohol, including 3 to 20 ethylene oxide moieties, polyoxyethylene-20 isohexadecyl ether, polyoxyethylene-23 glycerol laurate, PEG 80 sorbitan laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof.

Additional nonionic surfactants that can be used include water soluble alcohol ethylene oxide condensates, such as the condensation products of a secondary aliphatic alcohol containing between about 8 to about 18 carbon atoms in a straight or branched chain configuration condensed with between about 5 to about 30 moles of ethylene oxide. Such nonionic surfactants are commercially available under the trade name Tergitol from Union Carbide Corp., Danbury, Conn. Specific examples of such commercially available nonionic surfactants of the foregoing type are $C_{11}$-$C_{15}$ secondary alkanols condensed with either 9 moles of ethylene oxide (Tergitol 15-S-9) or 12 moles of ethylene oxide (Tergitol 15-S-12) marketed by Union Carbide Corp., (Danbury, Conn.).

Other suitable nonionic surfactants include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl condensed with about 9.5 moles of ethylene oxide per mole of nonyl phenol, dinonyl phenol condensed with about 12 moles of ethylene oxide per mole of phenol, dinonyl phenol condensed with about 15 moles of ethylene oxide per mole of phenol and diisoctylphenol condensed with about 15 moles of ethylene oxide per mole of phenol. Commercially available nonionic surfactants of this type include Igepal CO-630 (a nonyl phenol ethoxylate) marketed by ISP Corp. (Wayne, N.J.). Suitable non-ionic ethoxylated octyl and nonyl phenols include those having from about 7 to about 13 ethoxy units. Such compounds are commercially available under the trade name Triton X (Union Carbide, Danbury, Conn.).

Alkyl polyglycosides may also be used as a nonionic surfactant in the present cleansers. Suitable alkyl polyglycosides are known nonionic surfactants that are alkaline and electrolyte stable. Alkyl mono and polyglycosides are prepared generally by reacting a monosaccharide, or a compound hydrolyzable to a monosaccharide with an alcohol such as a fatty alcohol in an acid medium.

One example of such alkyl polyglycosides is APG™ 325 CS GLYCOSIDE, which is described as being a 50% $C_9$-$C_{11}$ alkyl polyglycoside, also commonly referred to as D-glucopyranoside. Another example of an alkyl polyglycoside surfactant is GLUCOPON™ 625 CS, which is described as being a 50% $C_{10}$-$C_{16}$ alkyl polyglycoside, also commonly referred to as a D-glucopyranoside. Both APG™ 325 CS GLYCOSIDE and GLUCOPON™ 625 CS are commercially available from Henkel Corp., Ambler, Pa.

Other useful nonionic surfactants include compositions based on amine oxides. One general class of useful amine oxides include alkyl di(lower alkyl) amine oxides in which the alkyl group has about 10-20, and preferably 12-16 carbon atoms, and can be straight or branched chain, saturated or unsaturated. The lower alkyl groups include between 1 and 7 carbon atoms. Examples include lauryl, dimethyl amine oxide, myristyl dimethyl amine oxide, and those in which the alkyl group is a mixture of different amine oxide, dimethyl cocoamine oxide, dimethyl (hydrogenated tallow) amine oxide, and myristyl/palmityl dimethyl amine oxide.

Another class of useful amine oxides include alkyl di(hydroxy lower alkyl) amine oxides in which the alkyl group has about 10-20, and particularly 12-16 carbon atoms, and can be straight or branched chain, saturated or unsaturated. Examples are bis(2-hydroxyethyl)cocoamine oxide, bis(2-hydroxyethyl) tallow amine oxide, and bis(2-hydroxyethyl) stearylamine oxide. Moreover, still other useful amine oxides include those characterized as alkylamidopropyl di(lower alkyl) amine oxides, in which the alkyl group has about 10-20 carbon atoms, and can be straight or branched chain, saturated or unsaturated. Examples are cocoamidopropyl dimethyl amine oxide and tallowamidopropyl dimethyl amine oxide.

Additional useful amine oxides include alkylmorpholine oxides in which the alkyl group has about 10-20 carbon atoms, and can be straight or branched chain, saturated or unsaturated. Further examples of amine oxides include those that commercially under the trade name AMMONYX (Stepan Co., Chicago, Ill.).

In addition to nonionic surfactants, the cleanser may also contain other types of surfactants. For instance, in some embodiments, amphoteric surfactants, such as zwitterionic surfactants, may also be used. For instance, one class of amphoteric surfactants that may be used in the present disclosure are derivatives of secondary and tertiary amines having aliphatic radicals that are straight chain or branched, wherein one of the aliphatic substituents contains from about 8 to 18 carbon atoms and at least one of the aliphatic substituents contains an anionic water-solubilizing group, such as a carboxy, sulfonate, or sulfate group. Some examples of amphoteric surfactants include, but are not limited to, sodium 3-(dodecylamino)propionate, sodium 3-(dodecylamino)-propane-1-sulfonate, sodium 2-(dodecylamino)ethyl sulfate, sodium 2-(dimethylamino)octadecanoate, disodium 3-(N-carboxymethyl-dodecylamino)propane-1-sulfonate, disodium octadecyliminodiacetate, sodium 1-carboxymethyl-2-undecylimidazole, and sodium N,N-bis (2-hydroxyethyl)-2-sulfato-3-dodecoxypropylamine.

Additional classes of suitable amphoteric surfactants include phosphobetaines and the phosphitaines. For instance, some examples of such amphoteric surfactants include, but are not limited to, sodium coconut N-methyl taurate, sodium oleyl N-methyl taurate, sodium tall oil acid N-methyl taurate, sodium palmitoyl N-methyl taurate, cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl) carboxymethylbetaine, oleyldimethylgammacarboxypropylbetaine, lauryl-bis-(2-hydroxypropyl)-carboxyethylbetaine, cocoamidodimethylpropylsultaine, stearylamidodimethylpropylsultaine, laurylamido-bis-(2-hydroxyethyl)propylsultaine, di-sodium oleamide PEG-2 sulfosuccinate, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium lauryl sulfosuccinate, disodium wheat germamido MEA sulfosuccinate, disodium wheat germamido PEG-2 sulfosuccinate, disodium isostearamideo MEA sulfosuccinate, cocoamphoglycinate, cocoamphocarboxyglycinate, lauroamphoglycinate, lauroamphocarboxyglycinate, capryloamphocarboxyglycinate, cocoamphopropionate, cocoamphocarboxypropionate, lauroamphocarboxypropionate, capryloamphocarboxypropionate, dihydroxyethyl tallow glycinate, cocoamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, cocamidopropyl betaine, lauric myristic amido propyl monosodium phosphitaine, and mixtures thereof.

In certain instances, it may also be desired to utilize one or more anionic surfactants within the cleansers. Suitable anionic surfactants include, but are not limited to, alkyl sulfates, alkyl ether sulfates, alkyl ether sulfonates, sulfate esters of an alkylphenoxy polyoxyethylene ethanol, alpha-olefin sulfonates, beta alkoxy alkane sulfonates, alkylauryl sulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amide polyoxyethylene sulfates, isethionates, or mixtures thereof.

Particular examples of some suitable anionic surfactants include, but are not limited to, $C_8$-$C_{18}$ alkyl sulfates, $C_8$-$C_{18}$ fatty acid salts, $C_8$-$C_{18}$ alkyl ether sulfates having one or two moles of ethoxylation, $C_8$-$C_{18}$ alkamine oxides, $C_8$-$C_{18}$ alkoyl sarcosinates, $C_8$-$C_{18}$ sulfoacetates, $C_8$-$C_{18}$ sulfosuccinates, $C_8$-$C_{18}$ alkyl diphenyl oxide disulfonates, $C_8$-$C_{18}$ alkyl carbonates, $C_8$-$C_{18}$ alpha-olefin sulfonates, methyl ester sulfonates, and blends thereof. The $C_8$-$C_{18}$ alkyl group can be straight chain (e.g., lauryl) or branched (e.g., 2-ethylhexyl). The cation of the anionic surfactant can be an alkali metal (e.g., sodium or potassium), ammonium, $C_1$-$C_4$ alkylammonium (e.g., mono-, di-, tri), or $C_1$-$C_3$ alkanolammonium (e.g., mono-, di-, tri).

Specific examples of such anionic surfactants include, but are not limited to, lauryl sulfates, octyl sulfates, 2-ethylhexyl sulfates, lauramine oxide, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, oleates, stearates, tallates, ricinoleates, cetyl sulfates, and similar surfactants.

Cationic surfactants, such as cetylpyridinium chloride and methylbenzethonium chloride, may also be utilized.

The specific surfactant(s) used in the cleansers of the present disclosure is not critical, but is preferably selected such that the cleanser will be mild to the skin and not strip essential oils from the hands when the cleanser is used. By providing a mild cleanser composition, the degree of skin irritation and cracking caused by frequent use of hand cleansers is reduced or eliminated.

Thus, in one aspect, the cleansers of the present disclosure comprise one or more mild surfactants. Certain surfactants are known to be extremely mild and/or to substantially lower the irritation potential of harsher or more irritating surfactants, such as certain surfactants known for their foaming properties. Mild surfactants are typically preferred to reduce the likelihood of the surfactant damaging the skin. Suitable mild surfactants include anionic surfactants such as sulfosuccinates, non-ionic surfactants such as decyl glucoside, amphoteric surfactants, such as cocamidopropyl betaine, and the like. Other suitable mild surfactants include disodium PEG-12 dimethicone sulfosuccinate, PEG-80 sorbitan laurate, polysorbate-20, lauroamphoglycinate, disodium cocamphodiacetate, disodium lauroamphodiacetate, sodium hydroxypropylphosphate laurylglucoside crosspolymer, sodium decylglucosides hydroxypropyl phosphate, sodium laurylglucosides hydroxypropylsulfonate, sodium cocoyl apple amino acids, non-ionic surfactants, such as PLURONIC surfactants, and combinations thereof. In one aspect, the cleanser may comprise only mild surfactants.

In other embodiments, one or more mild surfactant may be used in combination with one or more foaming surfactant. For instance, certain surfactants, while having good foaming properties, may also be harsh on the skin, particularly upon frequent use. Such surfactants may act to strip essential oils from the skin, leaving the skin feeling dry and tight. The negative effects of such surfactants may be mitigated by including these foaming surfactants into the cleanser of the present disclosure in combination with one or more mild surfactant. Inclusion of the mild surfactant in combination with harsher foaming surfactants acts to reduce the overall harshness of the cleanser, while still producing a cleanser having good foaming properties. Examples of suitable foaming surfactants for use in the cleansers of the present disclosure include anionic surfactants such as sodium lauryl sulfate, sodium laureth sulfate, sodium $C_{12}$-$C_{14}$ olefin sulfonate, and the like.

In certain embodiments, the surfactant present in the cleanser may comprise only a foaming surfactant. In these instances, it is generally preferable for the foaming surfactant to be included in lower amounts than would be needed if only mild surfactants were present in the cleanser or if a combination of mild surfactants and foaming surfactants was used. Alternately, the foaming surfactant may be included in the cleanser in combination with other cleanser ingredients, such as described herein, that may act to lessen the harshness of the foaming surfactant.

As noted above, the amount of surfactant contained in the cleanser can vary greatly depending upon various factors, such as type of surfactant, presence of other cleanser ingredients, and the like. Typically, however, the cleanser can contain surfactants in an amount of from about 0.01% (by weight of the cleanser) to about 70% (by weight cleanser). More suitably, the surfactant is present in the cleanser in an amount of from about 0.1% (by weight of the cleanser) to about 60% (by weight of the cleanser) and, even more suitably, from about 1% (by weight of the cleanser) to about 50% (by weight of the cleanser).

In addition to the surfactant, the cleanser can also include an emollient. As will be understood by those skilled in the art, certain surfactants, including some of the above described surfactants, may also function as an emollient. In these instances, the cleanser need not comprise an additional emollient, as the surfactant present in the cleanser may also perform that function. In other embodiments, however, the cleanser may further optionally include one or more emollient, which typically acts to soften, soothe, and otherwise moisturize the skin. Suitable emollients that can be incorporated into the cleansers of the present disclosure include oils such as petrolatum based oils, petrolatum, vegetable based oils, mineral oils, natural or synthetic oils, alkyl dimethicones, alkyl methicones, alkyldimethicone copolyols, phenyl silicones, alkyl trimethylsilanes, dimethicone, dimethicone crosspolymers, cyclomethicone, lanolin and its derivatives, fatty esters, glycerol esters and derivatives, propylene glycol esters and derivatives, alkoxylated carboxylic acids, alkoxylated alcohols, fatty alcohols, fatty acids, silicones, and combinations thereof.

Suitable esters could include, but not be limited to, cetyl palmitate, stearyl palmitate, cetyl stearate, isopropyl laurate, isopropyl myristate, isopropyl palmitate, and combinations thereof. The fatty alcohols could include but not be limited to octyldodecanol, lauryl, myristyl, cetyl, stearyl, behenyl alcohol, and combinations thereof. Ethers such as eucalyptol, ceteraryl glucoside, dimethyl isosorbic polyglyceryl-3 cetyl ether, polyglyceryl-3 decyltetradecanol, propylene glycol myristyl ether, and combinations thereof can also suitably be used as emollients.

The cleanser may include one or more emollient in an amount of from about 0.01% (by weight of the cleanser) to about 25% (by weight of the cleanser) and more desirably from about 0.1% (by weight of the cleanser) to about 20% (by weight of the cleanser).

The cleanser of the present disclosure may optionally further comprise a carrier. Non-limiting examples of suitable carrier materials include water; alcohols, including lower chain alcohols such as ethanol and isopropanol; hydrophilic bases such as glycerin, glycerin derivatives, and glycols such as polyethylene glycols, polypropylene glycols, propylene glycol, butylene glycol, ethoxydiglycol, and the like. Preferably, the carrier is water. In certain instances, the carrier may be present in the cleanser as water obtained from a blend of a surfactant active and water.

The cleanser may include a carrier in an amount of from about 0.01% (by weight of the cleanser) to about 99% (by weight of the cleanser) and more desirably from about 0.1% (by weight of the cleanser) to about 95% (by weight of the cleanser).

The cleanser may further comprise a moisturizer. Moisturizer present in the cleanser may advantageously be deposited on the skin upon use of the cleanser, thus helping to maintain lipids and essential oils present in the skin. Examples of suitable moisturizers include humectants; natural oils such as jojoba oil; synthetic oils such as mineral oil; silicones such as dimethicone; fatty alcohols and acids such as cetyl alcohol and stearic acid; waxes such as beeswax; and the like.

Particular examples of suitable humectants include glycerin, glycerin derivatives, sodium hyaluronate, hyaluronic acid, betaine, amino acids, glycosaminoglycans, honey, sorbitol, glycols such as propylene glycol, polyols, sugars, hydrogenated starch hydrolysates, salts of PCA such as sodium PCA, lactic acid, lactates, urea, and the like. A particularly preferred humectant is glycerin.

Other examples of suitable mositurizers include light hydrocarbon oil (e.g., mineral oil, isododecane, petrolatum), vegetable or natural oil (e.g., sunflower oil, olive oil, sweet almond oil, grapeseed oil, corn oil, safflower oil, shea butter, coconut oil, canola oil, castor oil, jojoba oil), hydrogenated vegetable oil (e.g., hydrogenated castor wax, hydrogenated apricot kernel oil, hydrogenated canola oil, hydrogenated jojoba oil, hydrogenated olive oil, hydrogenated sesame seed oil), waxes (e.g., beeswax, candelilla wax, carnauba, cerasin, hydrogenated microcrystalline wax, jojoba wax, microcrystalline wax, lanolin wax, ozokerite, paraffin, spermaceti wax), fatty ester (e.g., octyldodecyl neopentanoate, stearyl stearate, isopropyl myristate, isopropyl palmitate, stearyl behenate, $C_{12}$-$C_{15}$ alkyl benzoate, butyl isostearate, cetyl caprate, cetyl caprylate, ethyl apricot kernelate, ethyl avocadate, ethylhexyl caprate/caprylate, ethylhexyl cocoate, ethylhexyl isopalmitate, isocetyl myristate, isopropyl jojobate, myristyl laurate, isononyl isononanoate), fatty acid (e.g. palmitic acid, stearic acid, myristic acid, oleic acid, linoleic acid, behenic acid), fatty alcohol (e.g. lauryl alcohol, cetyl alcohol, stearyl alcohol, behenyl alcohol), silicones (e.g., dimethicone, cyclomethicone), polyethylene glycols, polypropylene glycols, or combinations thereof.

The cleanser of the present disclosure may suitably include one or more humectant or moisturizer in an amount of from about 0.01% (by weight of the cleanser) to about 25% (by weight of the cleanser), more desirably in an amount of from about 0.1% (by weight of the cleanser) to about 20% (by weight of the cleanser).

Optionally, the cleanser may further comprise particles capable of delivering moisturizers, emollients, or other skin benefit agents onto the skin. For instance, the cleansers may comprise particles loaded with moisturizers, humectants, emollients, or other beneficial agents that can be deposited on and remain on skin upon use of the cleanser. The presence of the particles may thus help increase the moisturizing ability of the cleanser, while providing a smooth skin feel.

Additionally, the particles may be used to enhance the effectiveness of the moisturizing liquid liner composition present on a treated glove, as described herein. Specifically, polymer particles deposited on the skin from use of the cleanser may have the ability to absorb moisturizers or oils present on the skin and/or in the moisturizing liquid liner composition. Thus, when a glove comprising the moisturizing liquid liner composition is placed on the hand of a user, moisturizers and oils present in the composition are absorbed by the particles and retained on the skin. The ability of the particles to absorb oils and other moisturizers present in the moisturizing liquid liner composition advantageously helps improve transfer of the composition to the skin of the glove wearer and allows for greater retention of the moisturizers on the skin and extended moisturization benefits.

In certain embodiments, the particles may be used deposit additional emulsifier onto the skin from the cleanser. The additional emulsifier may help enhance the amount of the moisturizing liquid liner composition that forms an emulsion upon wearing of the glove, thus improving the skin benefit effects of the composition. Examples of suitable emulsifiers include those described above for suitable for use in the moisturizing liquid liner composition.

Examples of suitable particles include those commercially available from Amcol Health & Beauty Solutions, Inc. and sold under the trade name POLYTRAP® 6603 (INCI Name; lauryl methacrylate/glycol dimethacrylate crosspolymer) and Polypore E-200 (INCI Name: allyl methacrylate crosspolymer). Other suitable particles include lipobeads. Lipobeads are composed of an internal cross-linked polymer network externally surrounded by a phospholipid bilayer. Examples of suitable lipobeads include those described in WO 2003/015701, herein incorporated by reference.

The cleanser may comprise particles in amounts of from about 0.01% (by weight of the cleanser) to about 10% (by weight of the cleanser) and desirably from about 0.1% (by weight of the cleanser) to about 5% (by weight of the cleanser).

In certain embodiments, the cleanser may further comprise other additional additives to improve a functional or physical property of the cleanser. For example, cleanser may further include an anti-bacterial agent. Examples of some suitable anti-bacterial agents for use in the cleanser can include sodium triclosan, triclocarban, quaternized ingredients such as benzalkonium chloride, benzethonium chloride, methylbenzethonium chloride, and combinations thereof quaternium compounds, biguanides, halogenated compounds, metal salts, and combinations thereof.

Typically, when an anti-bacterial is used, the cleanser can include from about 0.01% (by total weight of the cleanser) to about 10% (by total weight of the cleanser) disinfectant. More suitably, the cleansing composition can include from about 0.05% (by total weight of the cleanser) to about 5% (by total weight of the cleanser) disinfectant.

Another additive for use in the cleanser may be one or more non-aqueous solvents. Although not required, non-aqueous solvents can sometimes aid in dissolving certain components (e.g., preservatives, anti-microbial agent, etc.). Examples of some suitable non-aqueous solvents include, but are not limited to, glycerine; glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations thereof. Solvent combinations include a glycol, particularly hexylene and/or propylene glycol, and one or more lower alcohols, particularly isopropanol, n-propanol, and/or ethanol.

The cleanser can also include various preservatives to increase the shelf life of the cleanser. Some suitable preservatives that can be used in the present disclosure include, but are not limited to, Kathon CG, which is a mixture of methylchloroisothiazolinone and methylisothiazolinone available from Rohm & Haas; Mackstat H 66 (available from McIntyre Group, Chicago, Ill.); DMDM hydantoin (e.g., Glydant Plus, Lonza, Inc., Fair Lawn, N.J.); tetrasodium EDTA; iodopropynyl butylcarbamate; benzoic esters (parabens), such as methylparaben, propylparaben, butylparaben, ethylparaben, isopropylparaben, isobutylparaben, benzylparaben, sodium methylparaben, and sodium propyl-paraben; 2-bromo-2-nitropropane-1,3-diol; benzoic acid; amidazolidinyl urea; diazolidinyl urea; and the like. Other suitable preservatives include those sold by Sutton Labs, such as "Germall 115" (amidazolidinyl urea), "Germall II" (diazolidinyl urea), and "Germall Plus" (diazolidinyl urea and iodopropynyl butylcarbonate).

When utilized, the amount of the preservative present in the cleanser can generally vary depending on the relative amounts of the other components present within the composition. For example, in some embodiments, the preservative is present in the cleanser in an amount between about 0.001% (by weight of the cleanser) to about 5% (by weight of the cleanser), in some embodiments between about 0.001% (by weight of the cleanser) to about 1% (by weight of the cleanser), and in some embodiments, between about 0.01% (by weight of the cleanser) to about 1% (by weight of the cleanser).

In general, the pH of the cleanser may be controlled to be within any desired range, depending on the target soil. For example, a cleanser targeting an oily or greasy soil will desirably have a more basic pH. For bodily cleansing, it is typically desirable to have a cleanser with a neutral pH. If necessary, various pH modifiers may be utilized in the cleanser to achieve the desired pH level. For instance, some examples of basic pH modifiers that may be used in the cleanser include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium meta silicates; monoethanolamine; triethylamine; isopropanolamine; diethanolamine; and triethanolamine.

Moreover, some examples of acidic pH modifiers that may be used in the present disclosure include, but are not limited to, mineral acids; and carboxylic acids; and polymeric acids. Specific examples of suitable mineral acids are hydrochloric acid, nitric acid, phosphoric acid, and sulfuric acid. Specific examples of suitable carboxylic acids are citric acid, glycolic acid, lactic acid, maleic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly(methacrylic) acid, and naturally occurring polymeric acids such as carageenic acid, and alginic acid.

In one embodiment, the cleanser may additionally include one or more sequestrants. A sequestrant is a substance whose molecules can form one or more bonds with a metal ion. In particular, water often contains metal ions, such as calcium ions, that might react with anionic components (e.g., surfactants, acids, etc.) present within the cleansing composition. For example, in one embodiment, a surfactant that remains substantially unreacted with metal ions can better function as a cleansing agent.

Some examples of sequestrants that may be used in the cleansers of the present disclosure include, but are not limited to, ethylenediamines, ethylenediaminetetraacetic acids (EDTA) acid and/or salts thereof, citric acids and/or salts thereof, glucuronic acids and/or salts thereof, polyphosphates, organophosphates, dimercaprols, and the like.

Typically, when one or more sequestrants are used in the cleanser, the cleanser includes the sequestrants in an amount of from about 0.01% (by weight of the cleanser) to about 2.0% (by weight of the cleanser). More suitably, the cleanser includes from about 0.059 (by weight of the cleanser) to about 1.0% (by weight of the cleanser) sequestrant.

In order to better enhance the cleanser, other optional ingredients can also be used. For instance, some classes of ingredients that can be used include, but are not limited to: anti-microbial agents, antioxidants (product integrity); anti-reddening agents, such as aloe extract; astringents—cosmetic (induce a tightening or tingling sensation on skin); astringents—drug (a drug product which checks oozing, discharge, or bleeding when applied to skin or mucous membrane and works by coagulating protein); biological additives (enhance the performance or consumer appeal of the product); deodorants (reduce or eliminate unpleasant odor and protect against the formation of malodor on body surfaces); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); fragrances (consumer appeal); hydrotropes (helps dissolve some anti-microbial agents); opacifiers (reduce the clarity or transparent appearance of the product); skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); sunscreens and thickeners (to increase the viscosity of the formulation); fragrances; dyes; and the like.

In certain instances, it will be advantageous to formulate the cleanser to have a net non-ionic charge. Cleansers having a net non-ionic charge will typically be extremely mild on the skin, and provide a cleansing effect without stripping essential oils from the skin. In other instances, it may be advantageous to formulate the cleanser to have a cationic charge. Cationic charged cleansers will typically have a good moisturizer deposition on the skin from the cleanser, and may further help increase the degree of deposition of moisturizer from the moisturizing liquid liner composition present on the glove.

Hand Sanitizer

As noted above, the hand health and hygiene system of the present disclosure may further comprise a hand sanitizer. The sanitizer may provide an anti-bacterial, disinfection benefit to the user. In addition to acting as a disinfectant, the hand sanitizer may also be formulated to provide additional skin health benefits to a user, such as soothing, anti-irritant, and moisturization effects. The hand sanitizer may be used prior to or after use of the treated glove and/or hand cleanser.

Generally, the hand sanitizer for use in the hand hygiene regimen of the present disclosure can contain one or more disinfectants. The disinfectant contributes to the sanitizing effect of the sanitizer. In addition, the sanitizer can contain moisturizers, humectants, carriers, dyes, fragrances, chelating agents, rheology modifiers, thickeners, pH modifiers, and various other optional ingredients.

As described above, the hand sanitizer comprises one or more disinfectant. Suitable disinfectants include, for example, lower chain alcohols such as ethanol and isopropanol, quaternium compounds, biguanidines, halogenated compounds, and combinations thereof.

In preferred embodiments, the disinfectants are FDA approved or approved for use in the European Union. Examples of suitable FDA approved disinfectants are described in the Tentative Final Monograph for OTC Topical Antimicrobial Products (Federal Register, Jan. 6, 1978, 43 FR 1210: 1211-49, and in the Tentative Final Monograph for Healthcare Antiseptic Drug Products (Federal Register, Jun. 17, 1994, 59 FR 31402, 31402-52), herein incorporated by reference. It should be understood that the specific disinfectants and amounts thereof that are approved for use in the United States or European Union are subject to periodic change. As such, the specific examples and amounts set forth herein are not intended to be limiting.

For example, for a product marketed in the United States, preferred disinfectants and concentrations (reported as a percentage by weight of the sanitizer) may benzalkonium chloride in amounts from about 0.1% to about 0.13%, benzethonium chloride in amounts from about 0.1% to about 0.2%, methylbenzethonium chloride in amounts up to about 0.5%, hexylresorcinol, chlorhexidine gluconate in amounts up to about 0.5% to about % 4, parachloro-meta-xylenol in amounts up to about 0.24% to about 3.75%, chloroxylenol in amounts up to about 0.24% to about 3.75%, cloflucarban, fluorosalan, hexachlorophene in amounts up to about 0.1%, iodine complex (ammonium ether sulfate and polyoxyethylene sorbitan monolaurate), iodine complex (phosphate ester of alkylaryloxy polyethylene glycol), iodine tincture U.S.P., iodine topical solution U.S.P., nonylphenoxypoly (ethyleneoxy) ethanolidine, poloaxmer-iodine complex, triple dye, povidone-iodine complex in amounts up to about 5% to about 10%, undecoylium chloride iodine complex, mercufenol chloride, methylbenzethonium chloride, phenol greater than 1.5% aqueous/alcoholic, phenol less than about 1.5%, secondary amyltricresols, sodium oxychlorosene, tribromsalan, triclocarban, triclosan in amounts up to about 1%, calomel/oxyquinoline benzoate/triethanolamine/phenyl derivative combination, mercufenol chloride/secondary amyltricresols in 50 percent alcohol combinations, alcohols such as ethanol and/or isopropanol in amounts from about 60% to about 95%, and chlorohexidine gluconate. Combinations of these disinfectants may also be used.

The hand sanitizer may further comprise a moisturizer. The sanitizers of the present disclosure may advantageously be formulated such that moisturizer present in the sanitizer may be deposited on the skin upon use of the sanitizer, thus helping to maintain lipids and essential oils present in the skin, and preventing drying of the skin due to frequent sanitizer use. Examples of suitable moisturizers include humectants such as glycerin and propylene glycol; natural oils such as jojoba oil and sunflower oil; synthetic oils such as mineral oil and petrolatum; silicones such as dimethicone and cyclomethicone; fatty alcohols such as cetyl alcohol and cetearyl alcohol; fatty acids such as stearic acid and myristic acid; esters such as isopropyl palmitate and isononyl isononanoate; waxes such as beeswax; and the like. Other examples of suitable humectants and moisturizers include those described above as suitable for use in the hand cleanser.

The sanitizer of the present disclosure may suitably include one or more humectant or moisturizer in an amount of from about 0.01% (by weight of the sanitizer) to about 15% (by weight of the sanitizer), more desirably in an amount of from about 0.1% (by weight of the sanitizer) to about 10% (by weight of the sanitizer).

The sanitizer may further comprise a carrier. Non-limiting examples of suitable carrier materials include water; alcohols, including lower chain alcohols such as ethanol and isopropanol; hydrophilic bases such as glycerin, glycerin derivatives, and glycols such as polyethylene glycols, polypropylene glycols, propylene glycol, butylene glycol, ethoxydiglycol, and the like. Preferably, the carrier is water.

The sanitizer may include a carrier in an amount of from about 0.01% (by weight of the sanitizer) to about 99% (by weight of the sanitizer) and more desirably from about 0.1% (by weight of the sanitizer) to about 95% (by weight of the sanitizer). As will be understood by those skilled in the art, the specific amount of carrier present in the sanitizer will vary depending on the type of disinfectant used.

The sanitizer may further optionally comprise one or more emollients, sequestrants, non-aqueous solvents, preservatives, pH modifiers, anti-microbial agents, fragrances, dyes, rheology modifiers, thickeners, and various other optional ingredients. Specific examples and suitable amounts of these sanitizer components include those described above as suitable for use in the hand cleanser.

Methods

In one aspect, the present disclosure is further directed to a method for providing a skin benefit to hands and cleansing hands. The method comprises donning a treated glove, as described herein, cleansing the hands with a moisturizing hand cleanser of the present disclosure, and sanitizing the hands with a moisturizing hand sanitizer of the present disclosure.

The treated glove, moisturizer, and sanitizer may be used in any desirable combination. In one embodiment, the hands are cleansed and/or sanitized prior to donning the glove. In another embodiment, the method may further comprise removing the glove and cleansing and/or sanitizing the hands after removal of the glove.

Having described the disclosure in detail, it will be apparent that modifications and variations are possible without departing from the scope of the disclosure defined in the appended claims.

EXAMPLES

The following non-limiting examples are provided to further illustrate the present disclosure.

Example 1

In this example, a moisturizing liquid liner composition for use in combination with an article, such as a glove, of the present disclosure was prepared. The following ingredients were used to prepare the composition.

TABLE 1

| Ingredient | Function | Amount (% w/w) |
| --- | --- | --- |
| Polyglyceryl-4-isostearate; cetyl PEG-10/PPG-1 dimethicone; hexyl laurate | Emulsifier | 4.0 |
| Cyclomethicone | Carrier/emollient | 46.0 |
| Cetyl dimethicone | Carrier/emollient | 47.0 |
| Quaternium-80 | Skin conditioning | 1.0 |
| Dimethicone (350 cs) | Skin protectant | 2.0 |

The composition was prepared by mixing the ingredients together at room temperature until dispersed.

Example 2

In this example, the moisturizing liquid liner composition prepared in Example 1 was evaluated for its effect on skin moisturization when used in combination with a glove.

Sixteen (16) subjects between the ages of 18 and 68 were recruited for this study. Individuals with abnormal skin pigmentation at the test sites, skin disease, skin damage, skin damage due to sun exposure, tattoos or bruises on the testing areas of the arms, or excessive dryness or erythema were excluded. The subjects were instructed not to use skin creams, oils, ointment, powders, perfumes, or lotions on the hands less than 24 hours prior to and during testing.

On the day of testing, the subjects were acclimated to a temperature and humidity controlled room (70°±2° F.; 40%±5% relative humidity) for 15 minutes prior to baseline testing. After equilibration, baseline measurements were taken for skin moisture (conductance).

Baseline conductance measurements were taken at test sites on the back of the hands approximately 2 cm below the knuckles using a DermaLab Moisture Flat Probe (Cortex Technology, Hadsund Denmark). Conductance is the cosmetic industry standard for measuring moisture in the skin. The DermaLab Moisture Flat Probe was used for all measurements. It uses electrodes arranged as concentric rings to send a series of alternating electrical currents through the skin. Resistance to the currents indicates the water binding capacity of the stratum corneum, or moisture level, and provides a conductance reading. A higher conductance reading indicates a higher level of moisture in the skin. The instrument's probe was placed at the test site on the subject's hand and 5 second continuous measurements were taken in triplicate.

At the conclusion of baseline measurements, a glove was put on the hand of the subject. The gloves used in this test were nitrile gloves that were treated with either 0.015 g/g, 0.030 g/g, or 0.045 g/g add-on amount of the composition prepared in Example 1, or were controls containing no composition add-on. The gloves were worn for 10 minutes. The gloves were removed after 10 minutes and subjects were instructed to remain in the temperature/humidity controlled room for an additional 20 minutes to allow the perspiration from their hands to flash off. After this 20 minute wait, final conductance measurements were taken using the procedure described above. A comparison of conductance measurements for subjects that wore gloves having the different composition add-on amounts or untreated control gloves was made relative to the baseline conductance measurements. The results are shown in FIG. 1.

The results indicated that all treated gloves provided an increase in hand moisturization as compared to the untreated gloves. As can be seen from FIG. 1, the gloves containing the three different composition add-on levels provided a greater statistically significant increase in conductance over the untreated glove. Surprising, it was observed that the glove containing the low composition add-on level (i.e., 0.015 g/g) provided an equivalent increase in hand moisturization as the glove containing the high composition add-on level (i.e., 0.045 g/g), implying that only a small quantity of composition is needed on the glove to deliver a measurable skin health benefit.

Example 3

In this example, a moisturizing hand sanitizer of the present disclosure was prepared. The ingredients and amounts used to prepare the moisturizing hand sanitizer are set forth in Table 2.

TABLE 2

| INCI Name | Amount (% wt) |
|---|---|
| Glycerin | 2.00 |
| Hydroxypropylcellulose | 0.05 |
| Water | 30.05 |
| Carbomer | 0.41 |
| Aloe barbadensia leaf powder | 0.01 |
| Panthenol | 0.10 |
| SD alcohol 40-B | 65.23 |
| Tocopheryl acetate | 0.10 |
| Aminomethyl propanol | 0.13 |
| Fragrance | 0.12 |
| Dimethicone/petrolatum/lauryl methacrylate/glycol dimethacrylate crosspolymer | 1.80 |

The hand sanitizer was prepared using the following procedure. To begin, the carbomer was dispersed in the water, and the hydroxypropyl cellulose was dispersed in the glycerin along with the aloe powder. The two dispersions were combined, and the panthenol, SD alcohol 40-B, tocoperyl acetate, fragrance, and the dimethicone/petrolatum/lauryl methacrylate/glycol dimethacrylate crosspolymer were added. The pH of the resulting sanitizer was adjusted to a pH of from about 5.5 to about 7.0 using the amino propanol.

Example 4

In this example, the hand sanitizer prepared in Example 3 was evaluated for its effect on skin moisturization. A control hand sanitizer containing the same composition ingredients as the hand sanitizer prepared in Example 3, except containing 0% of the dimethicone/petrolatum/lauryl methacrylate/glycol dimethacrylate crosspolymer (hereinafter referred to as dimethicone/petrolatum blend) and 31.85 wt. % water, was also tested.

Conductance measurements were performed using the procedure described in Example 2, with the following modifications. During equilibration, three 3 cm×3 cm sites were demarcated on the volar aspect of each subject's forearms, and baseline conductance measurements were taken at these test sites.

At the conclusion of baseline measurements, 60 µL of a hand sanitizer, either the sanitizer prepared in Example 3 or the control hand sanitizer containing no dimethicone/petrolatum blend, was applied with a positive displacement pipette to a test site. Each test site received a different sanitizer according to a randomization schedule. The sanitizers were rubbed into the test site for approximately 10 seconds using a gloved finger. Each sanitizer was tested on six different test subjects for a total of six trials.

Conductance measurements were taken in triplicate at each test site after 30 minutes and again after 120 minutes using the procedure described above. Conductance measurements for each sanitizer tested were evaluated relative to the baseline conductance measurements. The results are shown in FIG. 2 as the average change in absolute conductance values for each sanitizer, as compared to baseline measurements.

Figure 2:
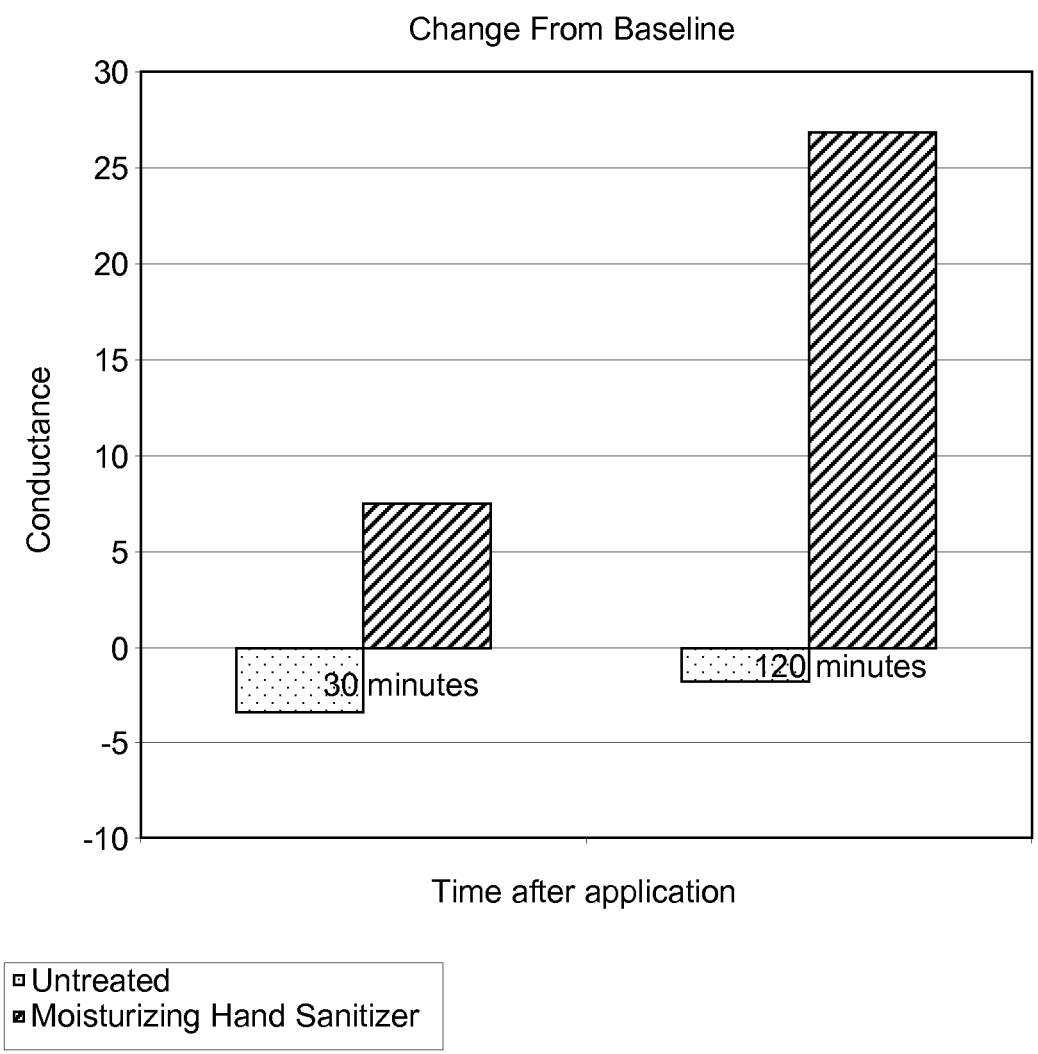
FIG. 2 is a chart illustrating the average change in absolute conductance measurements relative to a baseline measurement for moisturizing hand sanitizers comprising varying levels of a petrolatum/dimethicone blend, as described in Example 4.

As can be seen from FIG. 2, the sanitizer containing the moisturizing dimethicone/petrolatum blend showed statistically significant increases in moisturization over the control (shown as "untreated") containing no dimethicone/petrolatum blend at 30 and at 120 minutes. These results indicate that hand sanitizers that contain moisturizers may help enhance the moisturizing benefit of the hand health and hygiene system described herein.

Example 5

In this example, a moisturizing hand cleanser of the present disclosure was prepared. The following ingredients were used to prepare the cleanser.

TABLE 3

| Trade name | INCI name | Amount (% wt.) |
|---|---|---|
| Phase 1 | | |
| Water | Water | 60.45 |
| Plantaren 2000N | Decyl glucoside | 33.00 |
| Chlorhexidine gluconate | Chlorhexidine gluconate | 2.0 |
| Lamesoft PO 65 | Coco glucoside, glyceryl oleate | 3.00 |
| Cetiol HE | PEG-7 glyceryl cocoate | 0.75 |
| DMDM hydantoin | DMDM hydantoin | 0.20 |
| Phase 2 | | |
| Eumulgin L | PPG-1/PEG-9 lauryl glycol ether | 0.30 |
| Fragrance | Fragrance | 0.30 |
| Phase 3 | | |
| Potassium hydroxide 10% solution | Potassium hydroxide | q.s. |

The hand cleanser was prepared by adding together the Phase 1 ingredients, one at a time, and mixing each ingredient until homogenous. The Phase 2 ingredients were premixed until a clear solution was formed. The Phase 2 mixture was then added to the Phase 1 ingredients with mixing until homogenous. The pH of the resulting composition was adjusted to 6.0 to 7.0 using the potassium hydroxide, as needed.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above compositions and products without departing from the scope of the disclosure, it is intended that all matter contained in the above description shall be interpreted as illustrative and not in a limiting sense.

What is claimed is:

1. A hand health and hygiene system comprising:
a glove comprising an elastomeric substrate having a skin-contacting surface, and
a moisturizing liquid liner composition applied to at least a portion of the skin contacting surface, the moisturizing liquid liner composition comprising cetyl dimethicone, from about 30% to about 50% by weight of the moisturizing liquid liner composition comprises cyclomethicone,
dimethyl ditallow ammonium methylsulfate and an emulsifier,
wherein the emulsifier comprises polyglyceryl-4 isostearate, cetyl PEG/PPG-10/1 dimethicone and hexyl laurate,
wherein the moisturizing liquid liner composition is substantially anhydrous comprising about 5% or less by weight water, and
further wherein the moisturizing liquid liner composition is present on the skin-contacting surface in an add-on amount of from about 0.015 grams of the composition per grains of the glove (g/g) to about 0.045 g/g; and
a hand sanitizer comprising a moisturizer.

2. The system of claim 1 wherein the system further comprises a hand cleanser comprising a moisturizer.

3. The system of claim 2 wherein the moisturizing liquid liner composition is anhydrous.

4. The system of claim 1 wherein the moisturizing liquid liner composition further comprises dialkyl polysiloxanes comprising $C_4$ to $C_{22}$ alkyl groups.

5. The system of claim 2 wherein the moisturizing liquid liner composition comprises the emulsifier in an amount of from about 0.4% by weight of the composition to about 10% by weight of the composition.

6. The system of claim 1 wherein the moisturizing liquid liner composition comprises the dimethyl ditallow ammonium methylsulfate in an amount of from about 0.01% by weight of the composition to about 10% by weight of the composition.

7. The system of claim 2 wherein the moisturizing liquid liner composition further comprises dimethicone.

8. The system of claim 1 wherein the hand sanitizer comprises the moisturizer in an amount of from about 0.01% by weight of the sanitizer to about 15% by weight of the hand sanitizer.

9. A hand health and hygiene system comprising:
a glove comprising an elastomeric substrate having a skin-contacting surface, and
a moisturizing liquid liner composition applied to at least a portion of the skin contacting surface,
the moisturizing liquid liner composition comprising
cetyl dimethicone,
from about 30% to about 50% by weight of the moisturizing liquid liner composition cyclomethicone,
a dimethyl ditallow ammonium methylsulfate and an emulsifier,
wherein the emulsifier comprises polyglyceryl-4 isostearate, cetyl PEG/PPG-10/1 dimethicone and hexyl laurate,
wherein the moisturizing liquid liner composition is substantially anhydrous comprising about 5% or less by weight water, and
further wherein the moisturizing liquid liner composition is present on the skin-contacting surface in an add-on amount of from about 0.015 grams of the composition per grains of the glove (g/g) to about 0.045 g/g; and
a hand cleanser comprising a moisturizer.

10. The system of claim 9 wherein the moisturizing liquid liner composition further comprises dimethicone.

11. The system of claim 9 wherein the hand cleanser comprises a mild surfactant selected from a group consisting of sulfosuccinates, decyl glucoside, cocamidopropyl betaine, disodium PEG-12 dimethicone sulfosuccinate, PEG-80 sorbitan laurate, polysorbate-20, lauroamphoglycinate, disodium cocamphodiacetate, disodium lauroamphodiacetate, sodium hyroxypropylphosphate laurylglucoside crosspolymer, sodium decylglucosides hydroxypropyl phosphate, sodium laurylglucosides hydroxypropylsulfonate, sodium cocoyl apple amino acids, and combinations thereof.

12. The system of claim 9 wherein the hand cleanser comprises the moisturizer in an amount of from about 0.01% by weight of the hand cleanser to about 25% by weight of the cleanser.

13. The system of claim 1, wherein the hand sanitizer comprises a blend comprising dimethicone and petrolatum.

14. The system of claim 13, wherein the hand sanitizer comprises from about 0.5% to about 5% by total weight of the composition of the dimethicone and petrolatum blend.

* * * * *